US008823775B2

(12) United States Patent
Xu et al.

(10) Patent No.: US 8,823,775 B2
(45) Date of Patent: Sep. 2, 2014

(54) BODY SURFACE IMAGING

(75) Inventors: Bugao Xu, Austin, TX (US); Wurong Yu, Hixson, TN (US)

(73) Assignee: Board of Regents, The University of Texas System, Austin, TX (US)

( * ) Notice: Subject to any disclaimer, the term of this patent is extended or adjusted under 35 U.S.C. 154(b) by 911 days.

(21) Appl. No.: 12/771,565

(22) Filed: Apr. 30, 2010

(65) Prior Publication Data

US 2010/0277571 A1 Nov. 4, 2010

Related U.S. Application Data

(60) Provisional application No. 61/174,264, filed on Apr. 30, 2009.

(51) Int. Cl.
| | |
|---|---|
| H04N 13/02 | (2006.01) |
| G06T 7/00 | (2006.01) |
| G06T 17/20 | (2006.01) |
| G06T 17/00 | (2006.01) |
| A61B 5/00 | (2006.01) |

(52) U.S. Cl.
CPC ....... *G06T 17/20* (2013.01); *G06T 2207/10012* (2013.01); *G06T 7/0075* (2013.01); *G06T 2200/08* (2013.01); *G06T 17/00* (2013.01); *G06T 7/0057* (2013.01); *A61B 5/0077* (2013.01); *G06T 2207/30196* (2013.01)
USPC .................. 348/46; 348/47; 348/48; 348/51; 348/E13.074

(58) Field of Classification Search
USPC .......... 348/47, 48, 46, 51, E13.074; 396/324, 396/325
See application file for complete search history.

(56) References Cited

U.S. PATENT DOCUMENTS

| | | | |
|---|---|---|---|
| 4,737,032 A | 4/1988 | Addleman et al. | |
| 5,852,672 A | 12/1998 | Lu | |
| 5,864,640 A | 1/1999 | Miramonti et al. | |
| 5,953,448 A | 9/1999 | Liang | |
| 6,373,963 B1* | 4/2002 | Demers et al. | 382/108 |
| 6,968,075 B1* | 11/2005 | Chang | 382/154 |
| 7,065,242 B2 | 6/2006 | Petrov et al. | |
| 7,162,075 B2* | 1/2007 | Littlefield et al. | 382/154 |

(Continued)

OTHER PUBLICATIONS

Turk,G. and Levoy,M.[1994]. Zippered polygon meshes from range images, Proceedings of SIGGRAPH'94(Orlando, Fl, Jul. 24-29, 1994), ACM Press, pp. 311-318.*

(Continued)

*Primary Examiner* — Christopher S Kelley
*Assistant Examiner* — Ana Picon-Feliciano
(74) *Attorney, Agent, or Firm* — Trop, Pruner & Hu, P.C.

(57) ABSTRACT

An embodiment of the invention may provide a portable, inexpensive two-view 3D stereo vision imaging system, which acquires a 3D surface model and dimensions of an object. The system may comprise front-side and back-side stereo imagers which each have a projector and at least two digital cameras to image the object from different perspectives. An embodiment may include a method for reconstructing an image of a human body from the data of a two-view body scanner by obtaining a front scan image data point set and a back scan image data point set. A smooth body image may be gained by processing the data point sets using the following steps: (1) data resampling; (2) initial mesh generation; (3) mesh simplification; and (4) mesh subdivision and optimization.

17 Claims, 16 Drawing Sheets

(56) References Cited

U.S. PATENT DOCUMENTS

| | | | | |
|---|---|---|---|---|
| 2002/0085219 | A1* | 7/2002 | Ramamoorthy | 358/1.9 |
| 2004/0223640 | A1* | 11/2004 | Bovyrin | 382/154 |
| 2005/0190180 | A1* | 9/2005 | Jin et al. | 345/419 |
| 2008/0225042 | A1* | 9/2008 | Birtwistle et al. | 345/419 |
| 2008/0225045 | A1* | 9/2008 | Birtwistle et al. | 345/420 |
| 2009/0010507 | A1* | 1/2009 | Geng | 382/128 |

OTHER PUBLICATIONS

Agrawal, M.; Davis, L.S.; , "Window-based, discontinuity preserving stereo," Computer Vision and Pattern Recognition, 2004. CVPR 2004. Proceedings of the 2004 IEEE Computer Society Conference on , vol. 1, No., pp. I-66-I-73 vol. 1, Jun. 27-Jul. 2, 2004; doi: 10.1109/CVPR.2004.1315015.*

Weiyin Ma; Xiaohu Ma; Shiu-Kit Tso; Zhigeng Pan; , "Subdivision surface fitting from a dense triangle mesh," Geometric Modeling and Processing, 2002. Proceedings , vol., No., pp. 94-103, 2002 doi: 10.1109/GMAP.2002.1027500.*

Wurong Yu, et al., "Surface Reconstruction from Two-View Body Scanner Data," Textile Research Journal, 2008, pp. 1-11.

Bugao, Xu, et al., "Three-dimensional surface imaging system for assessing human obesity," Optical Engineering, Oct. 2009, vol. 48(10), pp. 1-1 to 1-11.

Wurong Yu, et al., "A portable stereo vision system for whole body surface imaging," Image and Vision Computing, 2009, 10 pages.

3D Surface Imaging Systems, "3dMD World Leader in High Precision 3D Surface Imaging Systems," 2007, 2 pages.

\* cited by examiner (a) (b) (c) (d)

(a) (b)

(a)  (b)

(a) (b) (c)

(a)  (b)  (c)

BODY SURFACE IMAGING

CROSS-REFERENCE TO RELATED APPLICATIONS

This application claims priority to U.S. Provisional Patent Application No. 61/174,264, filed on Apr. 30, 2009 and entitled "System and Methods for Three-Dimensional Surface Imaging and Measurement of the Human Body", the content of which is hereby incorporated by reference.

STATEMENT OF FEDERALLY FUNDED RESEARCH

The U.S. Government has certain rights in this invention pursuant to Contract No. 1R21DK081206-01 awarded by the NIH.

BACKGROUND

Generally, three-dimensional (3D) body surface imaging may be performed with a body scanner, which captures the surface geometry of the human body utilizing digital techniques. Body scanning provides noncontact, fast, and accurate body measurements. Anthropometric parameters computed by scanners include waist and hip circumferences, sagittal abdominal diameter, segmental volumes, and body surface area. Body-scanning technologies have evolved and several body scanners are commercially available. However, their high price and large size limit their practicality for field studies.

Body scanners may be based on, for example, (a) laser scanning, (b) structured light, or (c) stereo vision. In laser scanning, consecutive profiles may be captured by sweeping a laser stripe across the surface to be imaged. Laser scanning is more intricate and expensive than structured light or stereo vision methods as it may involve moving parts. Structured light may utilize a sequence of regular patterns to encode spatial information. It may require dedicated lighting and a dark environment, which makes the hardware relatively more complex than stereo vision. Also, with structure light systems images may need to be captured sequentially in synchronization with pattern projections. In the case of whole body scanning, image acquisition by structured light can be further slowed down because multiple sensing units in the system may not be able to work simultaneously; otherwise pattern projections from different units may interfere with each other. Stereo vision works similarly in concept to human binocular vision and is a passive method that it is not dependent on a light source.

Specifically regarding prior body imaging techniques, some scanners construct a 3D model of an object based on a series of silhouette and texture map images. Other scanners may obtain a 3D data set based on a grating pattern, having a sinusoidally varying intensity pattern, projected onto the surface of an object. The projected grating pattern may be shifted a number of times to generate data for the 3D model. Still other scanners may use phase measurement profilometry techniques for measuring the surface contour of an object having a surface discontinuity. Alternative scanners include a multiple view detector which is responsive to a broad spectrum of visible light. Other scanners use a pattern of vertical lines on the object-of-interest that appear to be bent differently to each camera by virtue of the surface shape of the object-of-interest and the relative geometry of the cameras. Additional scanners illuminate an object with a single plane of light producing a contour line that is viewed from two or more vantage points.

BRIEF DESCRIPTION OF THE DRAWINGS

Features and advantages of the present invention will become apparent from the appended claims, the following detailed description of one or more example embodiments, and the corresponding figures, in which:

FIGS. 7A and 7B are rectified image pairs; FIGS. 7C and 7D are coarse and refined disparity maps; and FIG. 7E is an image of the refined disparity map overlaid onto the reference image in an embodiment of the invention.

FIG. 12A is an image of the resampled and padded (in bold) data points in an embodiment of the invention.

FIG. 12B illustrates front and back meshes merged by tiling the modified contours in an embodiment of the invention. Frontal projections of the modified front and back contours, corresponding to the region marked with a dashed box in FIG. 12A, are shown in FIGS. 12C and 12D in an embodiment of the invention.

DETAILED DESCRIPTION

Figure 1:
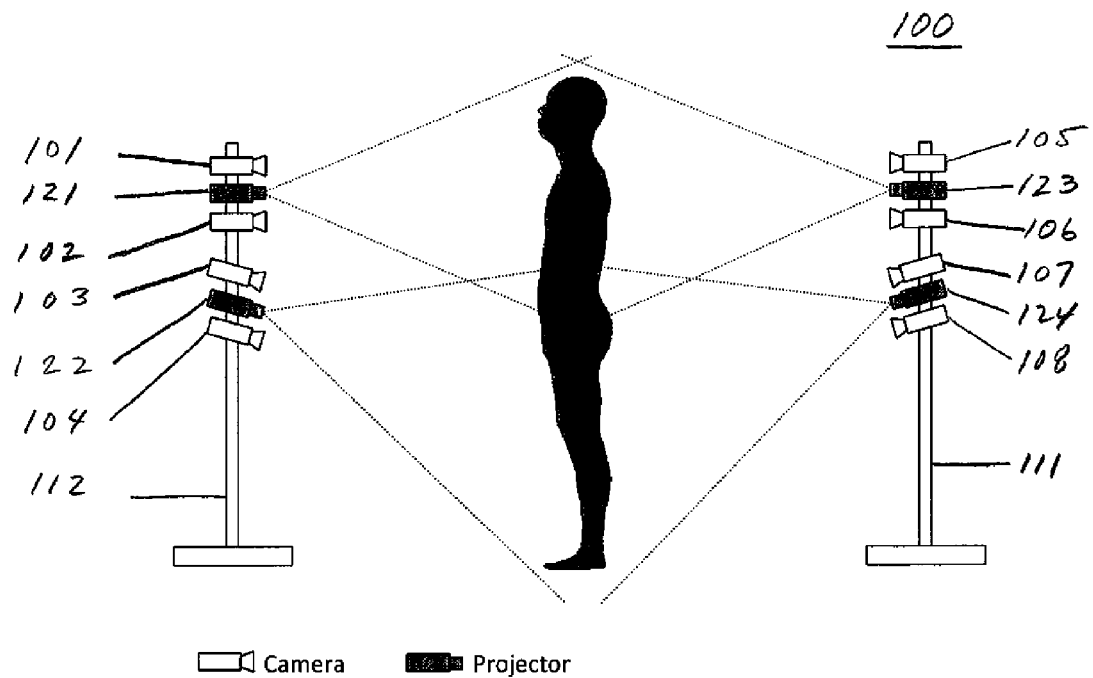
FIG. 1 is a schematic of a whole body scanner in an embodiment of the invention.

In the following description, numerous specific details are set forth. However, it is understood that embodiments of the invention may be practiced without these specific details. Well-known circuits, structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, steps, structures, or characteristics. Further, some embodiments may have some, all, or none of the features or steps described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. In the following description and claims, the terms "coupled" and "connected," along with their derivatives, may be used. "Connected" may be used to indicate that two or more elements are in direct physical or electrical contact with each other. "Coupled" may mean that two or more elements co-operate or interact with each other, but they may or may not be in direct physical or electrical contact.

An embodiment of the invention is more portable and affordable than current systems, and easy to calibrate, use and maintain. Stereo vision enables faster data acquisition and reduces system complexity compared to laser scanning and structured light technologies. Rapid data acquisition may be important to the curtailment of artifacts caused by body movements because a slight body position movement may induce unacceptable inaccuracy in quantification of body volume.

An embodiment may provide a 3D imaging system, which acquires a 3D surface model and dimensions of an object, having a stereo vision imaging system in communication with a computer system. The system may comprise a front-side stereo imager and a back-side stereo imager. The front-side stereo imager may have a front-side projector mounted to the front-side imager platform to cast a first random speck pattern onto an object to create a first artificial texture, and at least two front-side digital cameras to image the object and the first artificial texture from different perspectives. The back-side stereo imager may include a back-side projector mounted to the back-side imager platform to cast a second random speck pattern onto the object to create a second artificial texture, and at least two back-side digital cameras to image the object and the second artificial texture from different back-side perspectives.

An embodiment may include a method for reconstructing an image of a human body from the data of a two-view body scanner by obtaining a front scan image data point set in a front projection plane and a back scan image data point set in a back projection plane. The front scan image data point set may be resampled and each set of the front scan image data point set and the back scan image data point set may be triangulated. The front scan image data point set and back scan image data point set may be zippered or merged with an Add-Delete method to create an initial mesh. A control mesh may be created from the initial mesh to form a subdivision surface. The subdivision surface may be fitted to original data to optimize the control mesh and construct a piecewise smooth body model and a 3D body surface may be reconstructed from the piecewise smooth body model.

An embodiment provides a method of making a 3D surface model and dimensions of an object by generating a regular grid to explicitly extract information on a neighboring point using a stereo vision imaging system comprising a front-side stereo imager comprising a front-side projector (to cast a first random speck pattern onto an object to create a first artificial texture), and at least two front-side digital cameras (to image the object and the first artificial texture from different perspectives); and a back-side stereo imager comprising a back-side projector (to cast a second random speck pattern onto the object to create a second artificial texture), and at least two back-side digital cameras (to image the object and the second artificial texture from different back-side perspectives). The front-side projection data set and a back-side front projection data set are collected from the stereo vision imaging system. More than two data triangles may be formed by linear interpolation and triangulation among neighboring original data points of the front-side projection data set and the back-side front projection data set. The regular grid may be simplified by using quadric error metrics. The regular grid may be subdivided and optimized using a subdivision method to form a piecewise smooth mesh and the image may be rendered from the piecewise smooth mesh to reconstruct a 3D surface model.

An embodiment performs image acquisition, stereo matching, surface reconstruction, and body measurement. Image acquisition may involve camera synchronization and motion control. A stereo matching method may create 3D data from stereo images. A subdivision based surface reconstruction method may convert the 3D data points to a 3D body model. Body measurements may be performed to automatically obtain dimensions of the body.

An embodiment may include a stereo vision system. Two slightly separated cameras may reconstruct the visible surface of an object. Since the two cameras observe the object from slightly different views, the captured left and right images may not be exactly the same. The relative displacement of the object in the two images may be called the disparity, which may be used to calculate the depth. The system may include a stereo head that may consist of a pair of cameras (or more) and a projector. The projector may be used to shed artificial texture onto the body to be imaged. Multiple stereo heads may be used for full or partial body imaging. One, two, or more stereo heads may be used to cover each side of the body depending on the field of view of the cameras and projectors.

FIG. 1 is a schematic of a scanner in an embodiment of the invention. System 100 includes eight monochromatic CMOS cameras 101, 102, 103, 104, 105, 106, 107, 108. Various cameras may be used such as, for example, those from Videre Design, Menlo Park, Calif., each with a resolution of 1280× 960, focal length of 12 mm, and baseline length of 9 mm. Projectors 121, 122, 123, 124 may be, for example, NEC 575VT LCD projectors (NEC Corp., Tokyo, Japan), which are portable ultra-short throw projectors. At a projection distance of 2.3 m, the image size may be 1.5 m×1.15 m. Hence, when two such projectors are used together in embodiments of the invention, such as projectors 121, 122 or projectors 123, 124, with a slight overlap, the field of view may be as large as 1.5 m×2.0 m, which is large enough for the majority of population. A computer, such as the system described below in FIG. 24, may be used to control the cameras and projectors. The cameras may communicate with the computer via, for example, IEEE 1394 Firewire. Image acquisition or capture of subject 130 may be completed in a relatively instantaneous fashion. For example, image acquisition may occur in less than 200 ms, which may be considered to be relatively instantaneous. An NVIDIA GeForce 6500 dual-port graphics card may be used to send a texture pattern to the projectors through a VGA hub (Gefen Inc., Woodland Hills, Calif.).

Figure 2A:
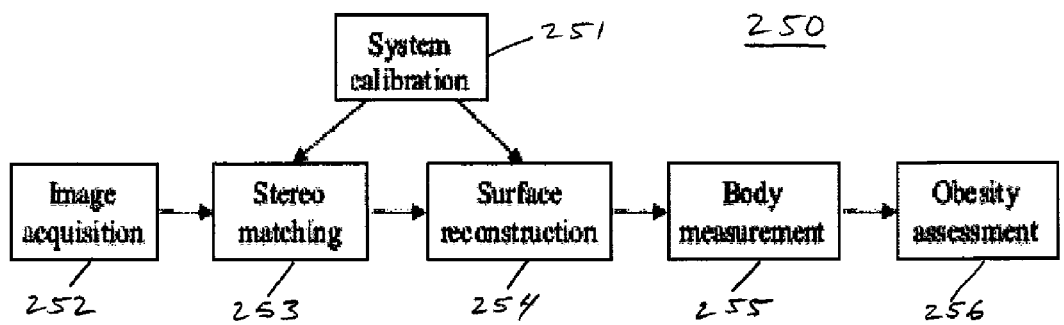
FIGS. 2a-b include flow charts for stereo matching in embodiments of the invention.

FIG. 2a includes a method 250 in an embodiment of the invention. In block 251 a system (e.g., system 100 of FIG. 1) is calibrated. In block 252 an image is acquired. Stereo matching occurs in block 253. Various embodiments of stereo matching are described below. In block 254 surface reconstruction occurs. Various embodiments of surface reconstruction are described below. In block 255 body measurements may be performed and in block 256 obesity assessments may be made. There are many versions of method 250 that include some, all, or additional blocks to those found in FIG. 2a. For example, blocks 255 and 256 may be optional. As another example, a provider may not acquire data but only process another party's data using, for example, block 253 and/or block 254 but not blocks 251 or 252.

Referring to FIGS. 1 and 2a, in an embodiment system 100 may be calibrated in numerous ways. For example, system 100 may be calibrated in two separate stages: camera calibration and 3D registration. Camera calibration may include determining the intrinsic and extrinsic camera parameters. The intrinsic parameters may correct distortion induced in each individual camera by imperfect lens and lens displacement, and may include the effective horizontal and vertical focal lengths, the principal point describing the center offset of the lens, and the radial and tangential lens distortion coefficients. The extrinsic parameters may describe the position and orientation of each individual camera in a reference coordinate system, and may be represented by a rotation matrix and a translation vector.

Based on the extrinsic parameters of the two cameras of a stereo head, their relative position and orientation may be determined. For example, a Small Vision System shipped with the cameras mentioned above may provide a toolbox of plane-based calibration routines, using various methods such as those described in Z. Zhang, "A flexible new technique for camera calibration," IEEE Trans. Pattern Anal. Mach. Intel., 22(11), 1330-1334 (2000)). The preceding camera calibration procedure may be performed separately on each individual stereo head, and each stereo head may have its own camera coordinate system.

3D registration may be used to transform each camera coordinate system to a common world coordinate system so 3D data from each view can be merged to complete surface reconstruction. This transformation may follow a rigid body model since the transformation may not change the Euclidean distance between any points. To determine a rigid body transformation, three noncollinear points may be sufficient. For example, a planar board target may be used. There may be six dots on each side of the board and each stereo head may require only three of them. The world coordinates of the centers of may be manually measured. The images of the target may be first rectified and then the dots may be identified and sorted. The centers of the dots may be estimated and the camera coordinates of each point may be calculated from its disparity.

In an embodiment it may not be necessary to repeat calibration frequently since the relative position of two cameras in a stereo head can be readily fixed and intrinsic camera parameters can be stabilized using locking lenses. Therefore, in some embodiments only 3D registration may be required when the system is transported. This may foster portability of the system and also reduce maintenance cost.

Figure 2B:
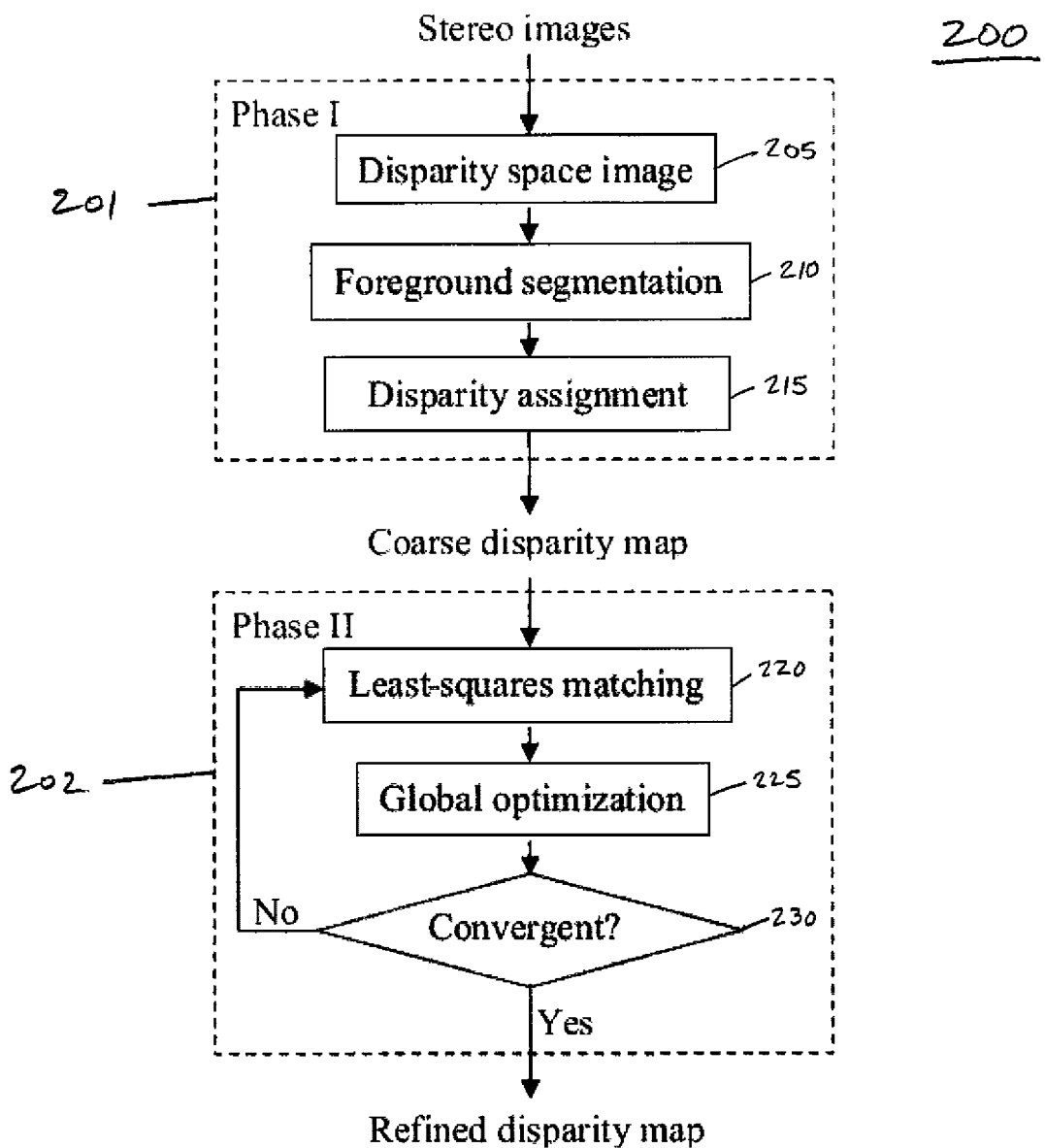
Figure 3:
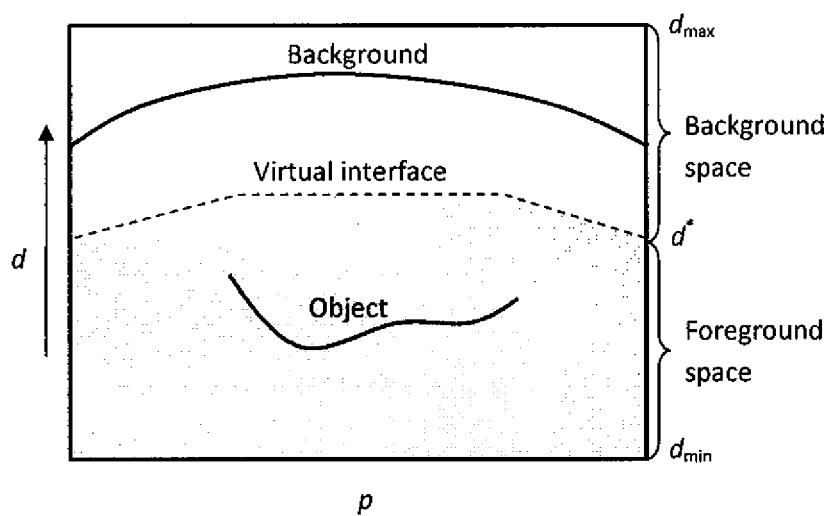
FIG. 3 is a schematic of the partition of the disparity space by an assumed virtual interface in an embodiment of the invention.

FIG. 2b includes a flow chart for a stereo matching method 200 in an embodiment of the invention. Stereo matching may solve disparity or correspondence problems in stereo vision. An embodiment may match images with sub-pixel accuracy to obtain 3D data of sufficient quality for body measurements. (Since embodiments of the invention may capture the front and rear sides of the body only, some portions of the body may be invisible to the cameras. To deal with this issue, a surface reconstruction method (addressed below) may be capable of filling in the gaps in 3D data caused by occlusions.)

In an embodiment stereo matching method 200 may include two phases indicated in blocks 201, 202. In block 201, foreground objects may be segmented from the background of the scene. A disparity map with integer-pixel accuracy may be computed. In block 202 the disparity map may be iteratively refined to reach subpixel accuracy.

More specifically, in block 205 a disparity space image (DSI) may be computed. A disparity space image (DSI) may be a matching cost function defined in the reference image and at each possible disparity. $I_l(x,y)$ and $I_r(x,y)$ may be designated the left and right intensity images, respectively. The left image may be taken as the reference and a match may then be denoted as $(x,y)_l \leftrightarrow (x+d(x,y),y)_r$ where $d(x,y)$ is the disparity map to be solved. When the images have been rectified so that the disparity exists only in the horizontal scanline, a match may be measured by normalized cross-correlation (NCC) since it is less sensitive to photometric distortions by the normalization in the local mean and standard deviation. Accordingly, the matching cost may be:

$$C(x,y,d) = 1 - \rho(x,y,d) \qquad (1)$$

where $\rho(x,y,d)$ is the NCC coefficient. Since $-1 \leq \rho(x,y,d) \leq 1$, $0 \leq C(x,y,d) \leq 2$. The trivariate function $C(x,y,d)$ may be called the DSI. For the sake of conciseness, the DSI may be denoted as $C_p(d)$ with p being a pixel.

In block 210 foreground segmentation may be performed in the DSI. P may denote the pixel set of the reference image. L={F, B} may be defined as a label set with F and B representing the foreground and background, respectively. One may then find a segmentation (or labeling) $f(P) \mapsto \rightarrow L$ that minimizes an energy function E(f) which may consist of two terms, $$E(f) = \sum_{i \in P} D_p(f_p) + \sum_{(p,q) \in N} V_{p,q}(f_p, f_q), \qquad (2)$$

where $N \subset P \times P$ is the set of all neighboring pixel pairs; $D_p(f_p)$ is derived from the input images that measure the cost of assigning the $f_p$ to the pixel p; and $V_{p,q}(f_p,f_q)$ imposes the spatial coherence of the labeling between the neighboring pixels p and q.

To derive $D_p(f_p)$ the disparity space may be divided into two subspaces: the foreground space and the background space that contain the object and the background, respectively. The interface between the two subspaces may be determined from the known geometrical configuration of the system. The interface may be denoted as d*(P).

$$C_p^F = \min_{d_{min} \le d \le d_p^*} C_p(d), C_p^B = \min_{d_p^* < d \le d_{max}} C_p(d),$$

and thus $C^F(P)$ and $C^B(P)$ represent the minimum surfaces in the foreground and background subspaces, respectively. If $C_p^F < C_p^B$ then there may be a heightened chance that the pixel p belongs to the foreground. The same applies to $C_p^B < C_p^F$ and the background. Therefore, $D_p(f_p)$ may be defined by $$D_p(f_p) = \begin{cases} C_p^F, & f_p = F \\ C_p^B, & f_p = B \end{cases}. \quad (3)$$

Since there are only two states in the label space L, the Potts model (see herein) may be used to define the spatial coherence term in Equation (2), i.e., $$V_{p,q}(f_p, f_q) = \begin{cases} \beta_{p,q}, & f_p \ne f_q \\ 0, & f_p = f_q \end{cases}. \quad (4)$$

In the 8-neighborhood system, one may set $\beta_{p,q} = \beta_0$ if p and q are horizontal or vertical neighbors, and $$\beta_{p,q} = \frac{\beta_0}{\sqrt{2}}$$

if they are diagonal neighbors.

As a binary segmentation problem, the global minimum of the energy function E(f) may be searched by using a graph-cuts method (See, e.g., V. Kolmogorov and R. Zabih, "Computing visual correspondence with occlusions using graph cuts," in Proc. IEEE Int. Conf. on Computer Vision, pp. 508-515, IEEE Computer Society, New York (1981)). Once the pixels are labeled, each pixel in the foreground may be assigned a disparity (block 215) to minimize the cost function, i.e., $$d(x, y) = \operatorname*{argmin}_d C(x, y, d) = \operatorname*{argmax}_d \rho(x, y, d). \quad (5)$$

The obtained disparity map may be noisy so, for example, median filtering may be used to quench the impulse noise. Furthermore, morphological close and open operators may be used to smooth the contour.

In one embodiment of the invention, in block 202 (second phase) the disparity map from block 201 (first phase) may only take discrete values, and thus in an embodiment it may be refined to achieve sub-pixel precision. The refinement process may be iterative and may involve two steps: local least-squares matching (block 220) and global optimization (block 225). For the first step (block 220), the amount of update is estimated locally for each pixel. The estimation may be made by minimizing the matching cost function defined in Equation (1). However, the process may be difficult since the NCC function p is highly nonlinear. Thus, in an embodiment the sum of squared differences (SSD) may be applied to define the matching cost as in a least-squares matching method (e.g., B. D. Lucas and T. Kanade, "An iterative image registration technique with an application to stereo vision," in Proc. DARPA Image Understanding Workshop, pp. 121-130, Washington, D.C. (2001). If the SSD takes into account the gain and bias factors between cameras, it may be essentially equivalent to NCC. Now the matching cost may be defined as $$C_{SSD}(x, y, d) = \sum_{(u,v) \in W(x,y)} (I_r(u+d, v) - (aI_l(u, v) + b))^2, \quad (6)$$

where W(x,y) is a matching window around (x,y), and a and b are the gain and bias factors, respectively. Then the local estimate of the disparity $\tilde{d}$ is obtained by minimizing the above equation.

In the second step (block 225), the disparity map may be optimized at a global level by minimizing the following energy function, $$E(d) = \iint (d(x,y) - \tilde{d}(x,y))^2 dx dy + \lambda \iint (d_x^2 + d_y^2) dx dy, \quad (7)$$

where $d_x$, $d_y$ are the disparity gradients. The first term of the function may measure the consistency with the local estimation, and the second term may impose smoothness constraints on the solution. $\lambda$ may be called the regularization parameter that weighs the smoothness term. This process may follow principles of regularization theory (e.g., T. Poggio, V. Tone, and C. Koch, "Computational vision and regularization theory," *Nature (London)* 317 (6035), 314-319 (1985)).

In block 230, steps 220, 221 may be repeated until a convergence is reached. High accuracy may be reached by the least-squares matching. Meanwhile, stability may be maintained and potential errors may be corrected by the global optimization.

Following stereo matching, surface reconstruction may occur (described herein and along with alternative embodiments described further below). The raw data obtained from stereo matching may be comprised of around 1 million scattered 3D points, from which it may be hard to read and handle the desired information directly. Surface reconstruction may be a process that accurately fits the raw data with a more manageable surface representation. Thus, the data may be manipulated and interpreted more easily for some specific applications. A proper surface representation may be selected initially. A representation may be the B-spline surface representation due to its properties such as piecewise smoothness, local support, and the same differentiability as found with the basis functions. But B-spline patches may require cylindrical or quadrilateral topology, and intricate boundary conditions may be necessary to zipper patch together to represent a more complex surface. In contrast, a piecewise smooth subdivision surface, resulting from iteratively refining a control mesh of arbitrary topology, may give a more flexible representation.

Since the system may be made up of four stereo heads mounted on two stands that are placed in front and in back of the subject, the scan data can be grouped into two sets that correspond to the front and back views, respectively. For a system (e.g., system 100 of FIG. 1), there may be large gaps in the data caused by occlusions. A data set may comprise over 1 million scattered 3D points. Embodiments of the invention may provide for surface reconstruction that creates an accurate, smooth, complete, and compact 3D surface model, which may be used in applications such as 3D body measurement. Embodiments may produce a surface that is a good approximation to the original data, as well as be capable of filling the holes and gaps and smoothing out noise.

In an embodiment, the original 3D data points on a regular grid may be resampled, and the explicit neighborhood information of these resampled data are utilized to create an initial dense mesh. Then the initial dense mesh may be simplified to produce an estimate of the control mesh. Finally, the control mesh may be optimized by fitting its subdivision surface to the original data, and accordingly, the body model may be reconstructed.

Thus, FIGS. 2a-b describe an embodiment for stereo matching and surface reconstruction. Following is a description of various additional embodiments for stereo matching and surface reconstruction.

FIGS. 3-10 address an embodiment of the invention for stereo matching. The stereo matching method may be used in a system such as system 100 of FIG. 1. A consideration in matching may be to choose a proper matching metric (similarity or dissimilarity measure between two corresponding pixels). One may let $I_l(x,y)$ and $I_r(x,y)$ be the left and right intensity images, respectively, with the left image taken as the reference image. To take into account unbalanced exposure, gain, and contrast of the camera pair, one may use a NCC as the similarity measure, which may be defined as $$\rho(x, y, d) = \frac{\sum_{(u,v) \in W(x,y)} (I_l(u, v) - \bar{I}_l(x, y))(I_r(u+d, v) - \bar{I}_r(x+d, y))}{N\sigma_l(x, y)\sigma_r(x+d, y)}, \quad (8)$$

where $W(x,y)$ may be a correlation window around $(x,y)$ with a total pixel number N, and $\bar{I}_l(x,y)$ ($\bar{I}_r(x,y)$) and $\sigma_l(x,y)$ ($\sigma_r(x,y)$) may be the local mean and standard deviation of intensity for the left (right) image. The normalization in the local mean and standard deviation may make NCC insensitive to photometric distortions. Based on $\rho(x,y,d)$, the cost function may be defined by $$C(x,y,d)=1-\rho(x,y,d) \quad (9)$$

Since $-1 \leq \rho(x,y,d) \leq 1$, one may have $0 \leq C(x,y,d) \leq 2$. $C(x,y,d)$ may be defined in the whole image space and at each possible disparity. This trivariate function may be termed the DSI One may denote the cost function as $C_p(d)$ with p being a pixel.

Foreground segmentation may be addressed next. Foreground segmentation may be related to a class of matching methods called layered stereo which may be effective in dealing with occlusions and discontinuities in the scene. Nevertheless, these existing methods may rely on color segmentation. However, some embodiments may have a natural scene appearance eclipsed by the projection of artificial texture, which may make it difficult to perform segmentation from color, contrast, or texture.

An embodiment may define an Energy Function to foster foreground segmentation considering. In other words, the problem of foreground segmentation can be formalized in the framework of energy minimization. One may let P denote the pixel set of the reference image. One may also define L={F, B} as a label set with F and B representing the foreground and background, respectively. Then the goal may be to find a segmentation (or labeling) $f(P) \mapsto L$ that minimizes an energy function E(f) defined on a given stereo image pair $I_l$ and $I_r$.

The energy function E(f) may consist of two terms, $$E(f) = \sum_{i \in P} D_p(f_p) + \sum_{(p,q) \in N} V_{p,q}(f_p, f_q), \quad (10)$$

where $N \subset P \times P$ is the set of all neighboring pixel pairs; $D_p(f_p)$ is derived from the input images that measures the cost of assigning the $f_p$ to the pixel p; and $V_{p,q}(f_p,f_q)$ imposes the spatial coherence of the labeling between the neighboring pixels p and q. Here one may derive $D_p(f_p)$ from the $DSIC_p(d)$. First, one may assume the disparity space can be divided into two subspaces: the foreground space and the background space that contain the object and the background, respectively, as shown in FIG. 1. A virtual interface may exist between the two subspaces, which may be denoted by d*(P). Now one may define $$C_p^F = \min_{d_{min} \leq d \leq d_p^*} C_p(d), \; C_p^B = \min_{d_p^* < d \leq d_{max}} C_p(d),$$

and thus $C^F(P)$ and $C^B(P)$ represent the minimum surfaces in the foreground and background spaces, respectively. If $C_p^F < C_p^B$, then one may expect there is a heightened chance the pixel p belongs to the foreground. The same applies to $C_p^B < C_p^F$ and the background. Therefore, one can define $D_p(f_p)$ by the plot in FIG. 3, which includes an image of the partition of the disparity space by an assumed virtual interface.

$$D_p(f_p) = \begin{cases} C_p^F, & f_p = F \\ C_p^B, & f_p = B \end{cases}. \quad (11)$$

However, the above definition may be invalid for pixels that cannot be matched. It may occur at occlusions, but can also happen in textureless regions that may be caused by shadows. For the unmatched pixels, one may assign constants to the $D_p(f_p)$, $$D_p(f_p) = \begin{cases} C_O^F, & f_p = F \\ C_O^B, & f_p = B \end{cases}. \quad (12)$$

Here one may set $C_O^B < C_O^B$ to favor the background, since one may assume that occlusions and shadows exist in the background.

Now the problem may be to compute the $DSIC_p(d)$, to determine the virtual interface d*(P), and to detect unmatched pixels. The computation of the $C_p(d)$ may be expedited by box filtering (e.g., C. Sun, Fast stereo matching using rectangular subregioning 3D maximum surface techniques, International Journal of Computer Vision 47 (1/2/3) (2002) 99-117) or running sum method (e.g., J.P. Lewis, Fast Template Matching, Vision Interface, 1995, pp. 120-123), both of which may have a time complexity that is independent of the size of matching window.

The d*(P) may not be available, since a user may lack the prior knowledge about the structure of the scene. But the virtual interface may be well defined based on the system configuration, which may be described below. For the moment, one may assume the d*(P) has been determined.

To detect unmatched pixels, one may use conventional methods based on block matching. In block matching, the disparity for each pixel may obtained by searching the minimum in the DSI, i.e., $$d_p = \underset{d}{\mathrm{argmin}} C_p(d), \quad (13)$$

which may be substantially equivalent to searching the correlation peak according to Equation (9). However, false matches may occur (e.g., because disparities may be undefined at occlusions) and matching also may fail in other regions due to, for example, image noise, geometric distortion, or insufficient texture. One may take the false matches as unmatched. In an embodiment three criteria may be used for deciding a good match. First, the variation of intensity in the matching window should be above a threshold $\sigma_t$, otherwise the definition of NCC (and thus the matching cost) may be unstable. Secondly, the correlation value may be greater than a threshold $\rho_t$. Thirdly, the match should pass the left-right check, which means it is also related to a correlation peak if one takes the right image as the reference. There may be a tradeoff in setting the parameters $\sigma_t$ and $\rho_t$: the larger they are, the more confident one may be in decided good matches, but the chance of missing good matches may also increase. $\sigma_t$ may be set above the noise level of image, and $\rho_t$ may be determined by such factors as, for example, noise level, degree of perspective distortion, size of matching window, and accuracy of image rectification. It may be hard to optimize these parameters by incorporating the above-mentioned factors so they may be set empirically.

Regarding the spatial coherence term in Equation (10), since there are only two states in the label space L, the Potts model (e.g., Y. Boykov, O. Veksler, R. Zabih, Fast approximation energy minimization via graph cuts, IEEE Transactions on Pattern Analysis and Machine Intelligence 23 (11) (2001) 1222-1239) may be used, i.e., $$V_{p,q}(f_p, f_q) = \begin{cases} \beta_{p,q}, & f_p \neq f_q \\ 0, & f_p = f_q \end{cases}. \tag{14}$$

In the 8-neighborhood system, one may set $\beta_{p,q} = \beta_0$ if p and q are horizontal or vertical neighbors, and $$\beta_{p,q} = \frac{\beta_0}{\sqrt{2}}$$

if they are diagonal neighbors.

In some embodiments success of the segmentation technique may depend to some extent or be based on a correct definition of the virtual interface that partitions the disparity space into the foreground and background subspaces. Here one may describe how to determine the virtual interface for the developed stereo vision system based on the effective imaging volume, which may be defined as the volume in which the body can be fully captured by the system. It may be located in between the two imaging stands 110, 111. According to the optical geometry of the system and the body sizes of the majority of population, the dimensions of the effective imaging volume may be set as 1200 mm×2000 mm×800 mm (width×height×depth), as illustrated in FIG. 4.

Figure 4:
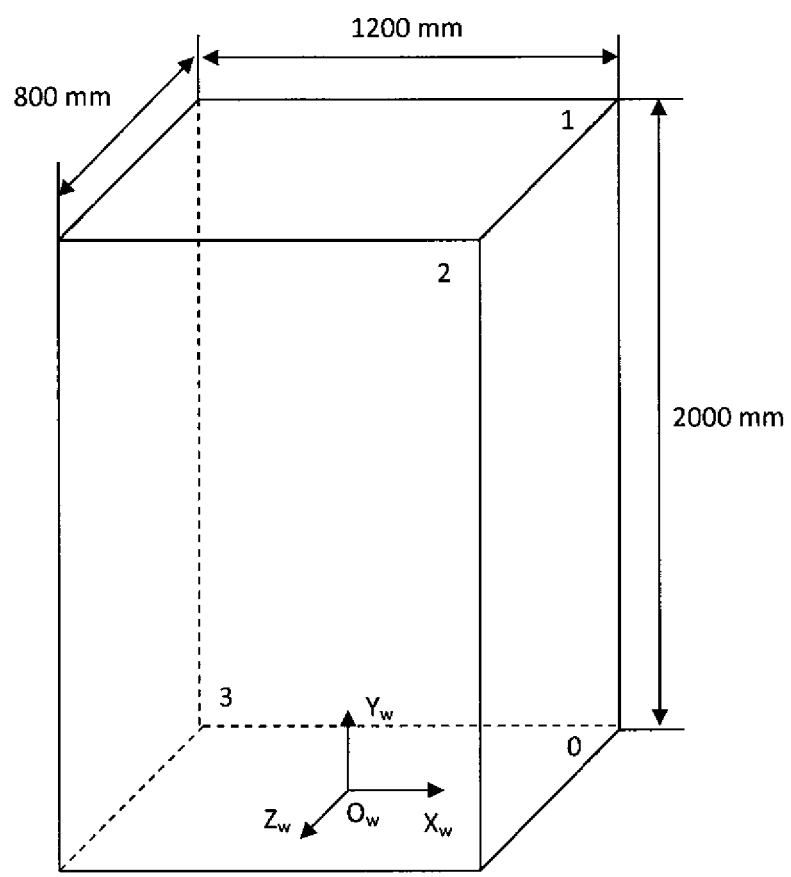
FIG. 4 is a schematic of the effective imaging volume of a stereo vision system in an embodiment of the invention.

FIG. 4 is an image of the effective imaging volume of the stereo vision system. The origin of the world coordinate system, $O_w$, is at the center of the floor plane of the volume, and the positive $Z_w$ axis points to the frontal stereo heads. The space within the volume may be clear except for the subject during imaging, and any external object may be ignored by embodiments of the matching method. Thus, one can use the virtual walls of the volume to divide the 3D space into the foreground and background. In practice, the two side walls may not be required because objects beyond them may be invisible to the cameras. The floor, roof, front and rear walls may be indexed from 0 to 3 in FIG. 4. For each stereo head, three of them may be applied to segment the foreground from the background. For example, the floor, roof and rear walls may be used for the frontal stereo heads.

One may need to convert the interface in the 3D space to the virtual interface in the disparity space. A problem may be how to compute the disparity map of a 3D plane. A 3D plane may induce a homography between the two image planes in stereo vision.

Figure 5:
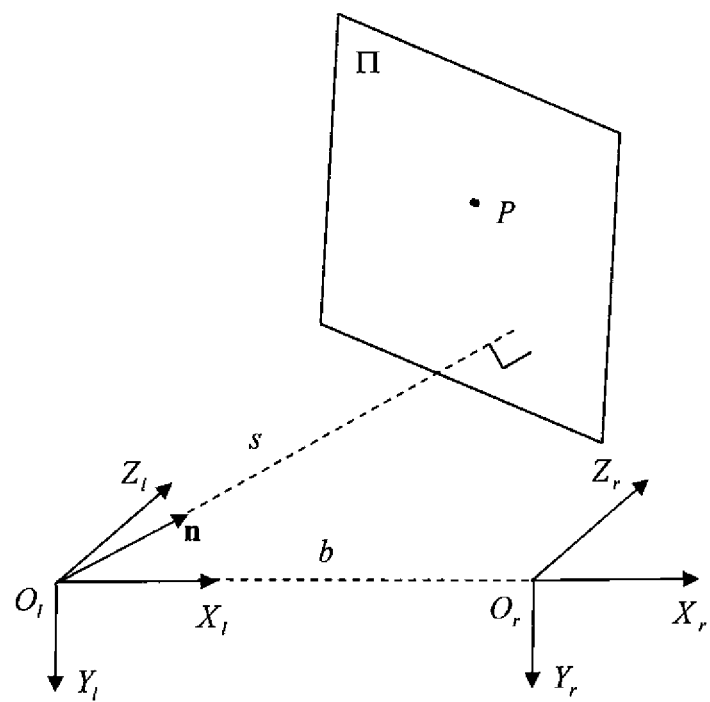
FIG. 5 is a schematic of two camera coordinate systems, with parallel-axis stereo geometry, in an embodiment of the invention.

In FIG. 5, two camera coordinate systems with the parallel-axis stereo geometry are defined. The 3D plane Π is defined in the left camera coordinate system with the normal n and the perpendicular distance from the origins. One may let $X_l$ and $X_r$ be the left and right camera coordinates respectively of an arbitrary point P in Π. The transformation between the two camera coordinate systems may be known, $$X_r = RX_l + t. \tag{15}$$

Since $n^T X_l = s$, i.e., $\frac{1}{s} n^T X_l = 1$.

FIG. 5 is an image of a 3D plane that induces a homography between the image planes in stereo vision.

$$X_r = RX_l + t\frac{1}{s}n^T X_l = \left(R + \frac{1}{s}tn^T\right)X_l = HX_l, \tag{16}$$

with $$H = R + \frac{1}{s}tn^T, \tag{17}$$

which is the homograph matrix associated with Π. Specifically, for the parallel-axis stereo geometry, $$R = I_3, t = \begin{bmatrix} -b \\ 0 \\ 0 \end{bmatrix},$$

and thus one has $$H = \begin{bmatrix} 1 - \frac{b}{d}n_x & -\frac{b}{d}n_y & -\frac{b}{d}n_z \\ 0 & 1 & 0 \\ 0 & 0 & 1 \end{bmatrix}. \tag{18}$$

Denote $$\tilde{x}_l = \begin{bmatrix} x_l \\ y_l \\ f \end{bmatrix} \text{ and } \tilde{x}_r = \begin{bmatrix} x_r \\ y_r \\ f \end{bmatrix},$$

which are the homogeneous coordinates of the projections of the point P in the left and right image planes, respectively. Then according to the perspective projection, one may obtain $\lambda_l \tilde{x}_l = X_l$, and $\lambda_r \tilde{x}_r = X_r$, where $\lambda_l$ and $\lambda_r$ are scalar values. In addition, one may have $\lambda_l = \lambda_r$ for the parallel-axis stereo geometry. Then by replacing $X_l$ and $X_r$ in Equation (16), one may obtain $$\tilde{x}_r = H\tilde{x}_l. \tag{19}$$

By combining Equations (18) and (19), one may have $$x_r = x_l - \frac{b}{s}[n_x \; n_y \; n_z]\begin{bmatrix} x_l \\ y_l \\ f \end{bmatrix} = x_l - \frac{b}{s}n^T \tilde{x}_l. \quad (20)$$

As a result, one can compute the disparity by $$d = x_r - x_l = -\frac{b}{s}n^T \tilde{x}_l. \quad (21)$$

It may be more convenient to define the plane H in the global world coordinate system, so one may need to transform it to each individual camera coordinate system in an embodiment of the invention. One may assume the plane equation in the world coordinate system is $$\hat{n}^T X_w = \hat{s}, \quad (22)$$

and the transformation between the camera and world coordinate systems are $$X_w = \hat{R} X_c + \hat{t}, \quad (23)$$

where one may assume the camera coordinate system is defined on the left camera, i.e., $X_c = X_l$. Then by inserting Equation (16) to Equation (15), one obtains $$(\hat{n}^T \hat{R}) X_c = \hat{s} - \hat{n}^T \hat{t}. \quad (24)$$

By comparing to $n^T X_c = s$, one obtains the plane parameters in the camera coordinate system, $$n = n^T \hat{R}, \quad (25)$$

and $$s = \hat{s} - \hat{n}^T \hat{t}. \quad (26)$$

The planes of the effective imaging volume in FIG. 4 are defined in Table 1. The floor plane has been slightly offset by 5 mm so as to separate the body from the floor.

TABLE 1

Planes of the effective imaging volume defined in the world coordinate system.

| | n̂ | ŝ (mm) |
|---|---|---|
| Plane 0 (floor) | $\begin{bmatrix} 0 \\ 1 \\ 0 \end{bmatrix}$ | 5 |
| Plane 1 (roof) | $\begin{bmatrix} 0 \\ 1 \\ 0 \end{bmatrix}$ | 2000 |
| Plane 2 (front) | $\begin{bmatrix} 0 \\ 0 \\ 1 \end{bmatrix}$ | 400 |
| Plane 3 (rear) | $\begin{bmatrix} 0 \\ 0 \\ -1 \end{bmatrix}$ | 400 |

Belief propagation and graph-cuts are methods to solve labeling problems in computer vision. However, belief propagation may only provide an approximate solution when there are loops in the graph (e.g., such as a two-dimensional image), even if the label space is binary. In contrast, generally exact minimum of the energy may be obtained by graph-cuts for a binary segmentation problem (M. Z. Brown, D. Burschka, G. D. Hager, Advances in computational stereo, IEEE Transactions on Pattern Analysis and Machine Intelligence 25 (8) (2003) 993-1008. Thus, one may use graph-cuts to perform the energy minimization of Equation (10). One may let $G=\langle V,E \rangle$ be a weighted graph. The set V may contain the nodes that correspond to the pixel set P and two additional nodes called terminals (the source s and the sink t). The nodes may be connected by the edges in the set E.

Figure 6:
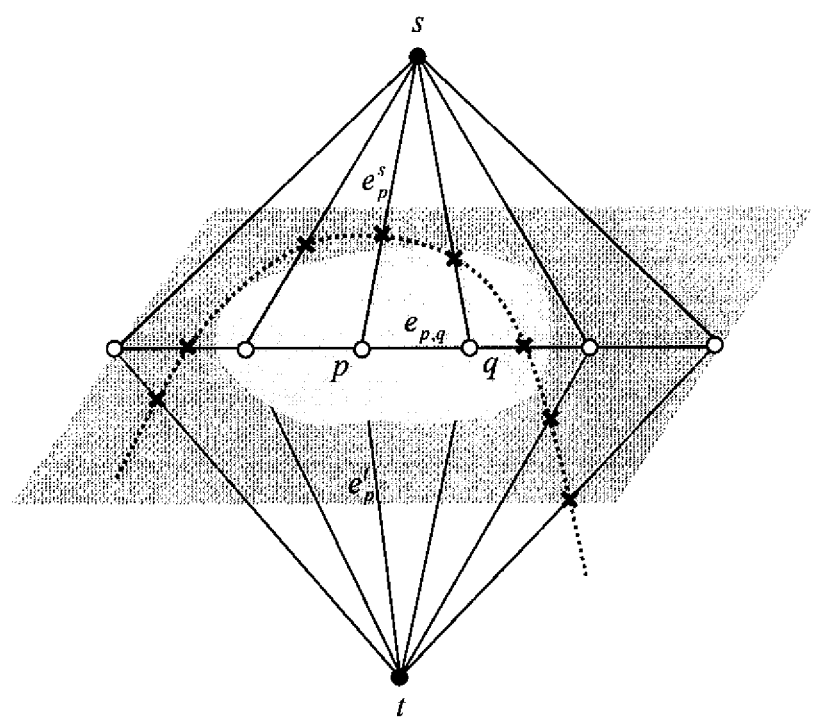
FIG. 6 is an image of a graph construction for energy minimization in an embodiment of the invention.

One may let s represent the foreground (F), and t be the background (B). As shown in FIG. 6, for each node that is associated to a pixel, say p, it may connect to s and t, and the edges as $e_p^s$ and $e_p^t$, respectively. For each pair of neighboring pixels, such as (p,q)∈N, one may connect the corresponding nodes and denote the edge as $e_{p,q}$. The edges may be assigned weights (costs) as follows: $c(e_p^s)=D_p(F)$, $c(e_p^t)=D_p(B)$, and $c(e_{p,q})=\beta_{p,q}$. A cut S|T may be defined as a partition of the nodes in V into two disjointed sets S and T, subject to s∈S and t∈T. The cost of S|T may be the sum of costs of all edges that go from S to T, $$c(S \mid T) = \sum_{p \in T} c(e_p^s) + \sum_{p \in S} c(e_p^t) + \sum_{p \in S, q \in T} c(e_{p,q}). \quad (27)$$

The sum of the first two terms in c(S|T) may correspond to the first term of the energy function in Equation (10), and the third term in c(S|T) may correspond to the second term of the energy function. Therefore, the cut S|T may be equivalent to a labeling f, and c(S|T)=E(f). As a result, to minimize the energy function may be generally equivalent to searching for a cut with the minimum cost. According to the theorem of Ford and Fulkerson (L. Ford, D. Fulkerson, Flows in Networks, Princeton University Press, 1962), the minimum cut problem can be solved by computing the maximum flow from the source to the sink. Some implementations of the maximum flow methods with polynomial complexities are available (e.g., Y. Boykov, O. Veksler, R. Zabih, Fast approximation energy minimization via graph cuts, IEEE Transactions on Pattern Analysis and Machine Intelligence 23 (11) (2001) 1222-1239; V. Kolmogorov, R. Zabih, Computing visual correspondence with occlusions using graph cuts, in: Proceedings of Eighth IEEE International Conference on Computer Vision (ICCV 2001), vol. 2, 2001, pp. 508-515).

FIG. 6 is an image of a graph construction for energy minimization. Once the foreground is segmented, its pixels may be assigned a disparity based on, for example, Equation (13). However, the obtained disparity map may be noisy. A median filter (e.g., T. S. Huang, Two-Dimensional Signal Processing II: Transforms and Median Filters, Springer-Verlag, Berlin, 1981) may be used to quench the impulse noise. Furthermore, morphological close and open operators (e.g., E. R. Dougherty, Hands-on Morphological Imaging Processing. Bellinghan, SPIE Press, Washington, 2003) may be used to smooth the contour.

The disparity map may take discrete values, from which the reconstructed surface may appear as staircases. A disparity refinement process may achieve sub-pixel precision. One methods is fitting a curve (e.g., parabolic or Gaussian curve) to the matching costs defined at discrete values. However, the curve fitting technique may suffer from systematic error called "pixel-locking" effect in which disparity values are pulled towards integers. Improvements have been made that focus on reducing the "pixel-locking" effect and make disparity refinement on each individual pixel independently. However, consistent with other local methods, the refined disparity map may be noisy. Thus, various embodiments take into account spatial coherence during disparity updating.

In an embodiment a method iteratively performs disparity refinement at a global level within a regularization framework (T. Poggio, V. Torre, C. Koch, Computational vision and regularization theory, Nature 317 (26) (1985) 314-319; D. Terzopoulos, Regularization of inverse visual problems involving discontinuities, IEEE Transactions on Pattern Analysis and Machine Intelligence 8 (4) (1986) 413-424). There may be two steps in each iteration: local estimation and global optimization. For the first step, the amount of update may be estimated locally for each pixel. The estimation may be made by minimizing the matching cost function defined in Equation (9), $$\delta d = \underset{\delta d}{\mathrm{argmin}} C(x, y, d + \delta d) = \underset{\delta d}{\mathrm{argmax}} \rho(x, y, d + \delta d), \quad (28)$$

where d is the current disparity value, and $\delta d$ is the amount to be updated. However, the process may be difficult since the correlation function $\rho$ is highly nonlinear. Although it is possible to perform linearization of $\rho$ with first-order approximation, the computation is still extensive. Thus, in embodiment applies the SSD as the matching cost as in Lucas-Kanade (B. D. Lucas, T. Kanade, An iterative image registration technique with an application to stereo vision, in: Proceedings of Imaging Understanding Workshop, 1981, pp. 121-130). If the SSD takes into account the gain and bias factors between cameras, it may be generally equivalent to normalized cross-correlation. Now the matching cost may be defined as $$C_{SSD}(x, y, d) = \sum_{(u,v) \in W(x,y)} (I_r(u + d, v) - (aI_l(u, v) + b))^2, \quad (29)$$

where a and b are the gain and bias factors, respectively. Here one may assume the disparity is constant within the matching window W. But this assumption may not be true except for frontal-parallel surfaces. To allow the disparity to vary within the window, one may first warp the right image based on the current disparity map, $$\hat{I}_r(x,y) = I_r(x + d(x,y), y). \quad (30)$$

To estimate $\delta d$, a and b, one may define an error function with $\hat{I}_r$ based on the SSD, $$e^2(\delta d, a, b; x, y) = \sum_{(u,v) \in W(x,y)} (\hat{I}_r(u + \delta d, v) - (aI_l(u, v) + b))^2. \quad (31)$$

With a first-order approximation:

$$e^2(\delta d, a, b; x, y) = \sum_{(u,v) \in W(x,y)} (\hat{I}_r(u, v) + \hat{I}_{rx}(u, v)\delta d - (aI_l(u, v) + b))^2, \quad (32)$$

where $$\hat{I}_{rx} = \frac{\partial \hat{I}_r}{\partial x}$$

is the intensity gradient of the warped right image. Let $p = [\delta d\ a\ b]^T$, $a = [I_{rx}\ -I_l\ -1]^T$, then a concise form of Equation (32) is $$e^2(p) = \Sigma(a^T p + I_r)^2. \quad (33)$$

This is a least squares problem. To minimize $e^2(p)$ is equivalent to solve the normal equations, $$Ap = b, \quad (34)$$

where $A = \Sigma a^T a$, and $b = -\Sigma I_r a$.

Thus, the above describes how to estimate $\delta d$ at each pixel. Below is addressed how to update the disparity map at a global level in an embodiment of the invention.

First, an energy function is defined by $$E(d) = \iint (d(x,y) - \tilde{d}(x,y))^{2dxdy + \lambda \iint} (d_x^2 + d_y^2) dxdy, \quad (35)$$

where $\tilde{d}$ is the local estimate of the disparity, and $d_x$, $d_y$ are the disparity gradients. The first term in the equation measures the consistency with the local estimation, and the second term imposes smoothness constraints on the solution. $\lambda$ is called the regularization parameter that weighs the smoothness term.

For the n-th iteration, one sets $\tilde{d}^n = d^{n-1} + \delta d^n$. Then the discrete form of E(d) can be expressed as $$E(d) = \sum_{(i,j) \in I} \left( (d^n(i, j) - (d^{n-1}(i, j) + \delta d^n(i, j)))^2 + \right. \quad (36)$$
$$\lambda((d^n(i+1, j) - d^n(i, j))^2 + (d^n(i, j+1) - d^n(i, j))^2)),$$

where (i,j) is the discrete coordinates of a pixel in the image plane I, and the discrete gradients are computed using the forward difference. Minimizing the energy function yields $$(1 + k_p \lambda)d_p^n - \lambda \sum_{q \in N(p)} d_q^n = d_p^{n-1} + \delta d_p^n \quad (37)$$

for each pixel p whose number of neighboring pixels is $k_p = |N(p)|$. The method can then establish a linear system $$Pd = h, \quad (31)$$

where $[P]_{p,p} = 1 + k_p \lambda$, $$[P]_{\substack{p,q \\ p \neq q}} = \begin{cases} -\lambda, & q \in N(p) \\ 0, & \text{otherwise} \end{cases},$$

$$[d]_p = d_p^n,$$

and $[h]_p = d_p^{n-1} + \delta d_p^n$.

Since P is a sparse, positive, symmetric matrix, the solution can be searched efficiently using the conjugate gradient method (J. R. Shewchuk, An Introduction to the Conjugate Gradient Method without the Agonizing Pain, Carnegie Mellon University, Pittsburgh, Pa., 1994).

Embodiments may utilize the above method to capture both static objects and human subjects for performance evaluation. A set of parameters, as listed in Table 2, may be used. FIGS. 7a-d show one such use in an embodiment of the invention.

Figure 7:
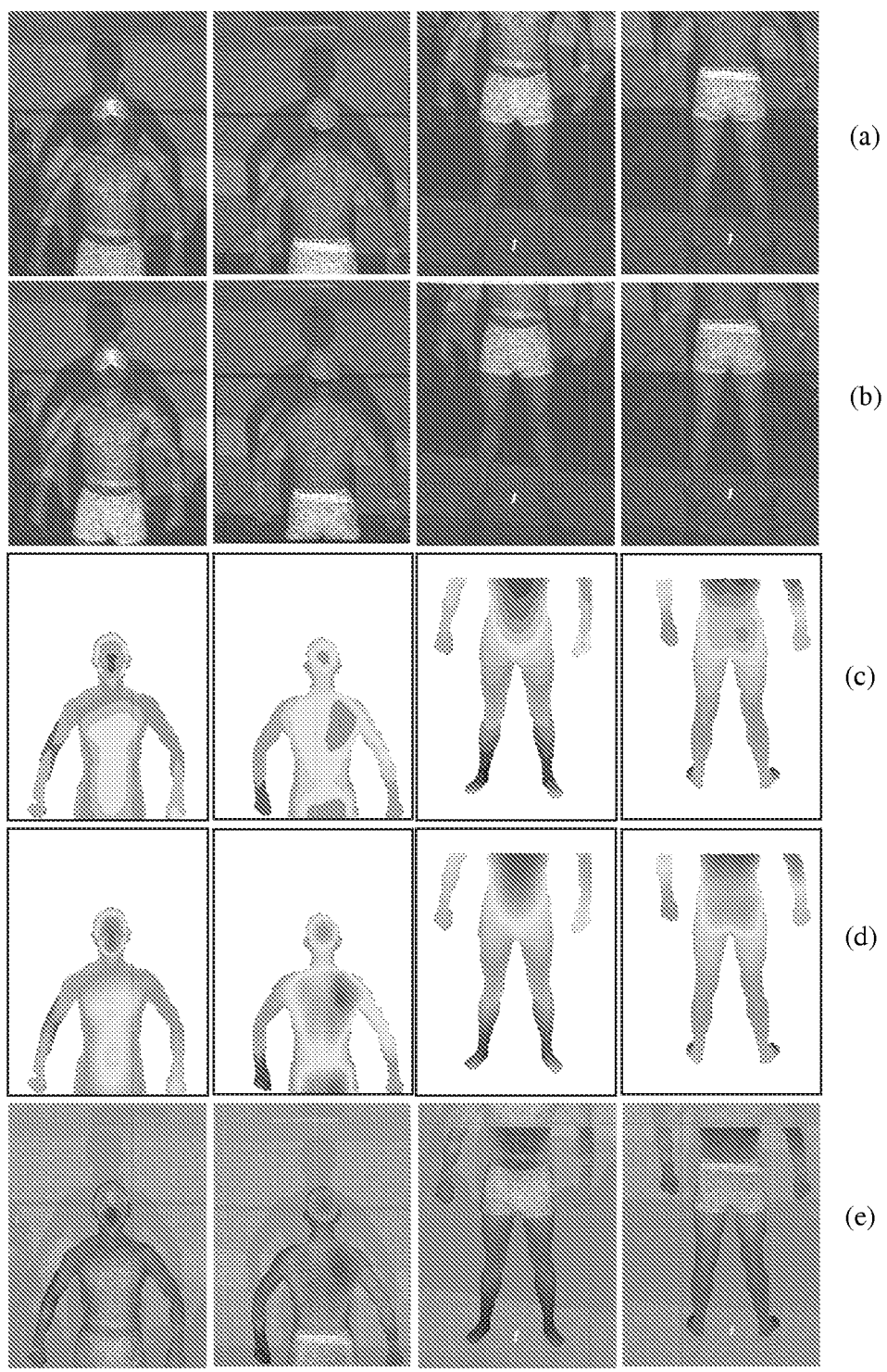
FIGS. 7A-7E are a series of images with four views of a human subject in an embodiment of the invention.

The virtual interface in the disparity space was created for each stereo head (see FIG. 1) according to its calibration parameters. The results on the four views of a human subject are shown in FIG. 7, where the rectified image pair is shown in FIGS. 7a and 7b; the coarse and refined disparity maps are shown in FIGS. 7c and 7d, respectively; and to better evaluate the performance of object segmentation, the refine disparity map has been overlaid onto the reference (left) image as shown in FIG. 7e. The disparities are coded with the standard cold-to-hot color mapping that corresponds to "far-to-close" to the cameras. The images and disparity maps have been rotated 90° clockwise for better display. Thus, embodiments of the method are capable of recovering geometric details and be effective in foreground segmentation even if the background is non-static and relatively complex.

TABLE 2

Parameters for the test of stereo matching.

| Parameter | Description |
|---|---|
| $W_{NCC} = 5 \times 5$ | Window size of NCC |
| $\sigma_t = 1.0$ | Threshold of the variation of intensity for detecting unmatched pixels |
| $\rho_t = 0.6$ | Threshold of NCC for detecting unmatched pixels |
| $C_O^F = 1.0$ | Cost of assigning an unmatched pixel to the foreground |
| $C_O^B = 0.2$ | Cost of assigning an unmatched pixel to the background |
| $\beta_0 = 1.0$ | Parameter in the Potts model |
| $W_{Median} = 21 \times 21$ | Window size of the median filter for reducing noise in the coarse disparity map |
| $r_{STE} = 3.3$ | Radius of the circular structural element in the morphological close operator for smoothing the contours of foreground objects |
| $N_{Iter} = 15$ | Number of iterations in disparity refinement |
| $W_{SSD} = 11 \times 11$ | Window size of SSD in disparity refinement |
| $\lambda = 10.0$ | Regularization parameter in disparity refinement |

Figure 8:
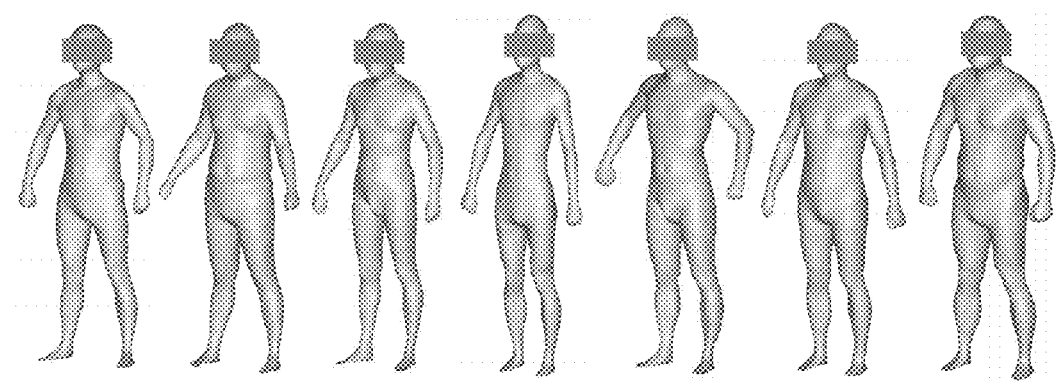
FIG. 8 is an image of the body models captured by a system in an embodiment of the invention.
Figure 9:
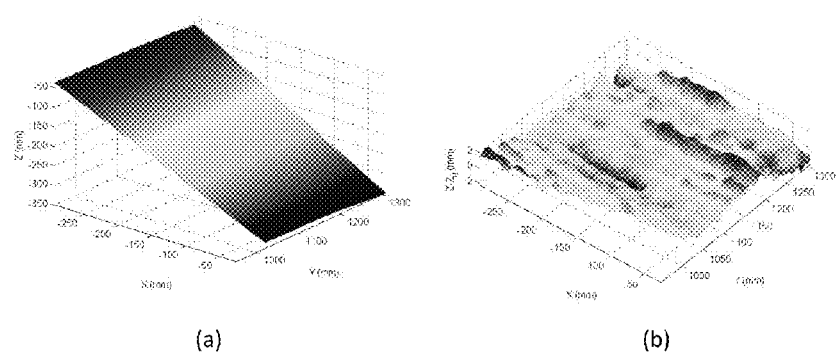
FIGS. 9A and 9B are images of the 3D surface imaging of a planar target in an embodiment of the invention.

FIG. 8 is an image of the examples of body models captured by an embodiment of the invention. A disparity map may be converted into a 3D point cloud by Equation (9), and then a complete 3D surface model can be reconstructed by merging point clouds from all four stereo heads. The surface reconstruction method developed for a two-view body scanner was modified. In this method, a 3D model is reconstructed by fitting a subdivision surface to the raw data.

To quantitatively estimate the matching precision, a planar surface target was placed at the center of the effective imaging volume and imaged by one of the stereo heads in an embodiment of the invention (FIG. 1). A region with a size of around 250 mm×200 mm was used for surface fitting, and the residual errors were used as a measure of matching precision. The results are displayed in FIG. 9. The standard deviation of the residual errors is about 0.7 mm, which provides an estimate of depth resolution of the system.

Figure 10:
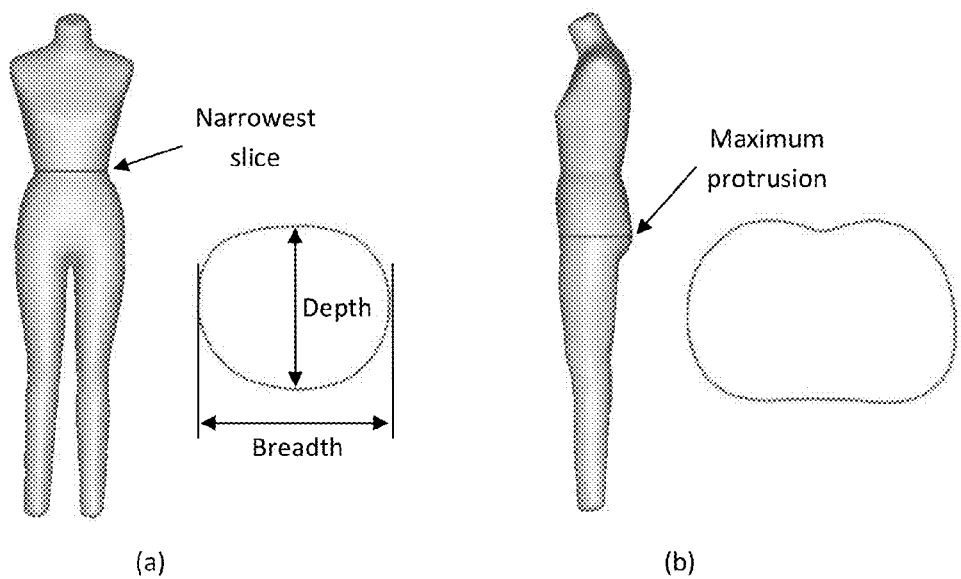
FIGS. 10A and 10B are images of a mannequin to measure waist and hip circumferences in an embodiment of the invention.

To evaluate the overall accuracy of the system, it was tested on a mannequin, which is a size-12 Wolf body form widely used for apparel design. A MyoTape body tape measure (AccuFitness, LLC, Greenwood Village, Colo.) was used to measure the waist and hip circumferences, and an anthropometer (Lafayette Instrument Company, Lafayette, Ind.) was used to measure the depth and breadth of the waist. The waist and hip were located according to the criteria as indicated in FIG. 10. The mannequin was imaged 10 times with repositioning in a given hour period. The waist and hip circumferences, and waist breadth and depth were measured on 3D data automatically.

FIGS. 11-24 are now discussed in relation to surface reconstruction. An embodiment includes a method based on subdivision surface representation for reconstruction of the human body from the data of a two-view body scanner (FIG. 1). In the case that the scan data can be grouped into front and back views, an embodiment of the invention (a) rearranges the data by resampling in the frontal projection plane, (b) triangulates each set of data points, and (c) zippering the front and back contours with an Add-Delete method to create an initial mesh. The initial mesh is simplified to produce a control mesh as the base of a subdivision surface. The control mesh is optimized by fitting its subdivision surface to the original data, and accordingly, a piecewise smooth body model is reconstructed. Embodiments are capable of gap and hole filling, are robust to noise, and are computationally efficient.

In body modeling, a proper surface representation may be required. Conventional methods may use the B-spline surface representation due to its properties such as piecewise smoothness, local support, and the same differentiability as with the basis functions. But B-spline patches may require cylindrical or quadrilateral topology, and intricate boundary conditions may be needed to zipper patches together to represent a more complex surface. In contrast, embodiments of the invention may use a piecewise smooth subdivision surface resulting from iteratively refining a control mesh of arbitrary topology to give a more flexible representation.

The scanner system of FIG. 1 includes two scanning units placed in front and back of the subject so that the scan data can be grouped into two sets which correspond to the front and back views, respectively. An advantage of the two-view scanner lies in its portability and low cost. However, large gaps exist between the two views due to occlusions. An output of the scanner, shown in FIG. 11, comprises about 36,000 scattered 3D points. The data are incomplete, non-uniformly distributed, and have outliers. Embodiments of the invention may create an accurate, smooth, complete and compact 3D surface model which not only produces a surface which is a good approximation to the original data, but which is also capable of filling the holes and gaps and smoothing out noise.

Figure 11:
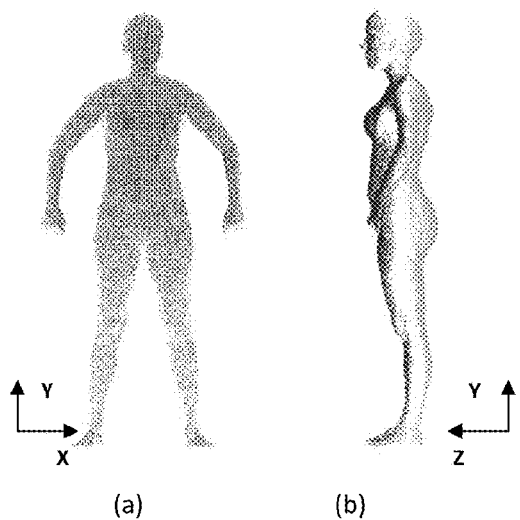
FIGS. 11A and 11B are original scan data of a subject in the anterior and lateral views, respectively.

As indicated above, an embodiment comprises four steps: (1) data resampling; (2) initial mesh generation; (3) mesh simplification; and (4) mesh subdivision and optimization. Regarding resampling, an initial mesh is generated from the scan data, which can be complicated when the data are noisy, incomplete and irregularly distributed. Thus, the data are resampled on a regular grid and then explicit neighborhood information can be easily extracted. The data set of both the front and back views can be regarded as samples on a bivariate surface defined in the frontal projection plane, i.e., the x-y plane in the (x,y,z) Cartesian coordinates as shown in FIG. 11. The projections of the data in the x-y plane may have irregular distributions because of the varying scanning resolution across the body. Data resampling may include methods which reorganizes the data on a regular grid defined in the x-y plane.

An embodiment may select grid density (i.e., the sampling intervals in the x and y directions) with sampling intervals such as, for example, $$\Delta y = \frac{y_{max} - y_{min}}{1.2 \times N},$$

and $\Delta x = \Delta y/1.5$, where $y_{min}$ and $y_{max}$ are the minimum and maximum y values, and N is the average of the numbers of scanlines in the front and back views. A smaller $\Delta x$ may be selected considering the original data are much denser in the x direction.

At each grid point, the z value may be estimated by linear interpolation among neighboring original data points. The neighborhood information may be obtained by triangulation on each data set. Due to the defects of the original data and the irregular contour of a human body, embodiments may use the partially organized characteristic of the scanlines to perform triangulation between each pair of neighboring scanlines. Since a scanline may come from different parts of the body (e.g., arms and torso) a threshold may be needed to determine whether two adjacent points in a scanline should be connected. The threshold may be set to be three times the mean horizontal distance between adjacent points. The local criterion for creating a triangle may be the minimum edge length. Once the triangulation is completed, a method may be used to perform linear interpolation. Triangles may be traversed to check if they hit a grid point or not. A triangle may hit more than one grid point. If a grid point is hit by a triangle, then its z value may be estimated by a linear combination of the three vertices of the triangle. If a grid point is not hit by any triangle, then it may be marked as an empty point. It can be seen that the output of resampling may actually be a range image for each data set.

In case the data are not arranged as scanlines (i.e., they are unorganized), an alternative method may be used for resampling. For each grid, all points falling in each cell may be collected and then one may compute the mean or median z value of the points as the z value of the grid point. This more general method may be computationally effective.

Regarding initial mesh generation, prior to mesh generation an embodiment preprocesses the resampled data to fill holes and remove outliers. First, the method defines a mask for each view. The mask may actually be a binary version of the range image; 1's may be assigned to the occupied grid points, and 0's to the empty points. Then the front and back masks may be combined by a logical "OR" operation. Small blobs in the combined mask may be removed as outliers, and the largest connected region may be kept as the body. If there are holes in the remaining region, they may be filled by flooding. The combined mask may serve as a reference in the following triangulation process.

The neighborhood information may be explicit in a range image, and a triangle mesh can be produced by triangulation between adjacent rows of data, which is similar to the triangulation procedure used above. When the front and back meshes are merged the mesh contours may be so irregular that some conventional tiling methods may fail. Accordingly, an Add-Delete method may be used.

In an Add-Delete method some points are added or "padded" to both range images according to the combined mask so that their contours have the same projection in the x-y plane. The z values of the added points may be set by interpolating their nearest neighbors. With this procedure, holes may also be filled. Then triangulation may be performed separately on both modified range images. To merge the two triangle meshes, the modified contours may be tiled by simply connecting corresponding points. When the meshes are merged, a vertex collapse method may be used to delete these added points. In vertex collapse, a vertex may be removed, and its adjacent vertices may be re-triangulated to form a new mesh. Small weights may be assigned to the added points, and consequently these points may get deleted first, possibly using a soft deletion method, in the following mesh simplification phase.

Figure 12:
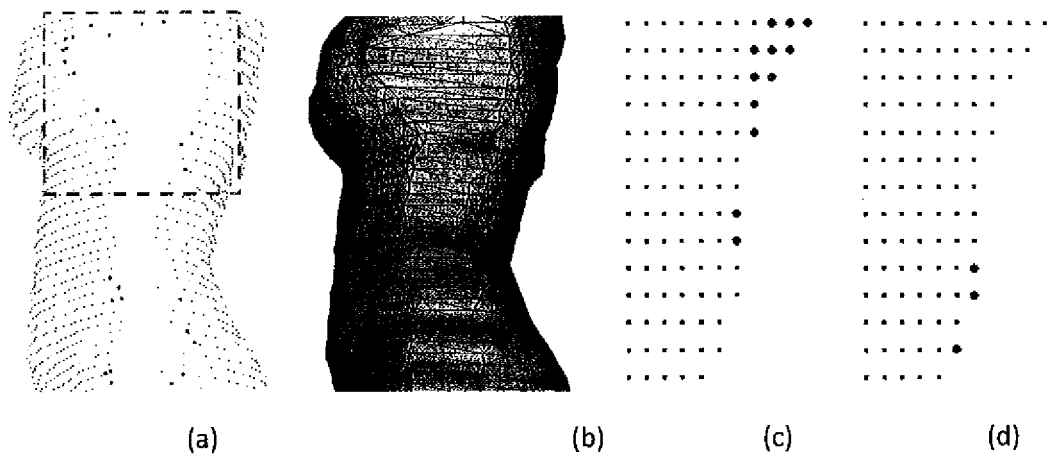
FIGS. 12A-D represent the triangulation of the torso.
Figure 13:
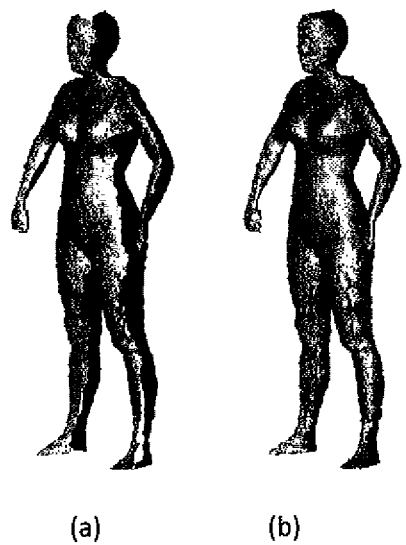
FIGS. 13A and 13B are images that show the generation of the initial mesh in an embodiment of the invention.

An example of the above mesh triangulation is shown in FIG. 12 wherein the bolded dots are added points. The frontal projections of the front and back meshes completely overlap after adding points. The generated initial mesh of the whole body is shown in FIG. 13. Gaps are closed after merging the contours.

As a brief aside, webbing is briefly addressed. A webbing effect can occur when different body segments are in close proximity or even touching (e.g., crotch and armpits of overweight subjects). Accordingly, an embodiment includes an interactive edit tool with which the user can manually mark an area where the webbing affect is likely to occur. Original data points in the marked area may be temporarily discarded for initial mesh generation stage, but may be used in the mesh optimization stage for surface fitting.

Figure 14:
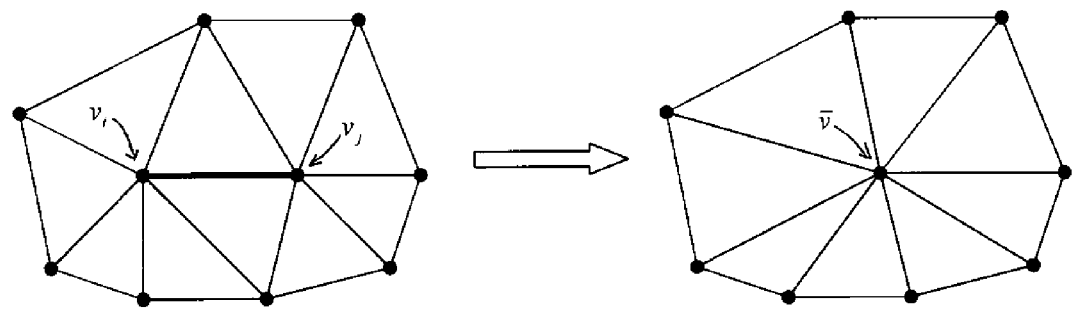
FIG. 14 shows an edge collapse where a new vertex is created by collapsing the edge in an embodiment of the invention.

Regarding mesh simplification, such simplification helps reduce the number of triangles and create a control mesh for the model. The method of simplification devised by Garland may be employed (Garland, M, "Quadric-based Polygonal Surface Simplification", PhD Thesis, Carnegie Mellon University, School of Computer Science, 1999). This method may produce high-quality approximations by using quadric error metrics and may be realized by edge collapse as shown in FIG. 14, where the new vertex $\bar{v}$ is evaluated by minimizing the weighted sum of its squared distances (the cost of contraction) to all triangles around vertices $v_i$ and $v_j$. An edge with the smallest cost of contraction may be collapsed first.

The quadric measure of the distance of a point v to a plane determined by a point p and a unit normal n is given by $$D^2(v)=((v-p)^T n)^2 = v^T n n^T v - 2(nn^T p)^T v + p^T n n^T p. \tag{39}$$

If $A=nn^T$, $b=nn^T p$, and $c=p^T nn^T p$, then the quadric error metric can be expressed as $$Q(v)=v^T A v - 2b^T v + c, \tag{40}$$

where the quadric Q is defined as a triple $$Q=(A,b,c). \tag{41}$$

The quadric for a given vertex v in the original mesh can be expressed as a weighted sum of the fundamental quadrics of its adjacent faces, $$Q = \sum_k w_k Q_k, \tag{42}$$

where $Q_k$ is the quadric of the kth adjacent face, and the associated weight $w_k$ is set as the face area.

For an edge to be collapsed, such as the edge $(v_i, v_j)$ in FIG. 13, the quadric is $Q=Q_i+Q_j$ and the cost of contraction is $Q(\bar{v})=Q_i(\bar{v})+Q_j(\bar{v})$, where $\bar{v}$ is the new vertex after collapse. By minimizing the function, one can get the optimal position of $\bar{v}$, $$\bar{v}=A^{-1}b, \tag{43}$$

and the cost $$Q(\bar{v})=-b^T A^{-1} b + c. \tag{44}$$

In an embodiment, all candidate edges are sorted in a heap based on costs. At each step, the edge with minimum cost may be removed from the heap and collapsed, and then the heap may be updated. This procedure may be iteratively repeated until enough simplification is achieved. To realize the aforementioned "soft deletion" strategy, the cost for an artificially added vertex may be scaled down so that its associated edges will move upwards in the heap and gain a higher priority for collapse.

Figure 15:
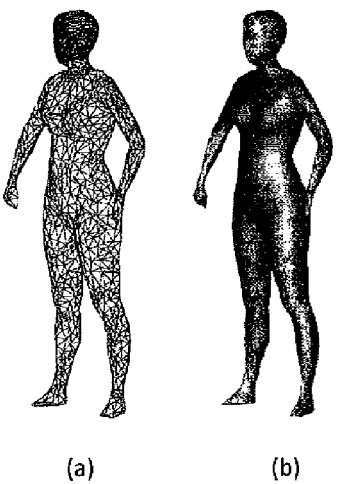
FIGS. 15A and 15B show a simplified control mesh and its shaded model in an embodiment of the invention.

An example for mesh simplification is shown in FIG. 15, where the mesh was obtained by collapsing 80% edges of the model in FIG. 13B. The mesh may serve as a control mesh for the surface subdivision described below.

Figure 16:
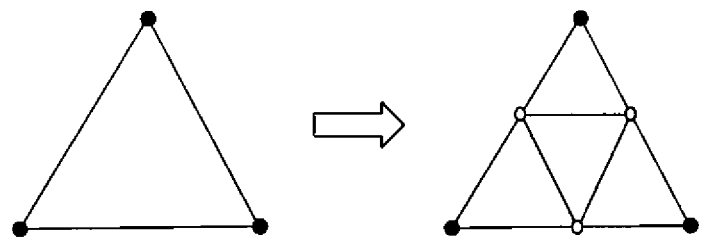
FIG. 16 shows a mesh subdivision by edge split in an embodiment of the invention.

Regarding mesh subdivision and optimization, embodiments of this method have a piecewise smooth mesh produced by surface subdivision techniques. Loop's subdivision method (Loop, C., "Smooth Subdivision Surfaces Based on Triangles", Master's Thesis, University of Utah, Department of Mathematics, 1987), by which a $C^2$ smooth surface can be obtained in the limit of infinite numbers of subdivisions. This method may be based on edge split, as shown in FIG. 16. In an embodiment, at each level of subdivision each edge is split into two and thus each face is split into four. The surface obtained by an infinite refinement process may be called the limit surface of the control mesh. A single level of subdivision may be enough to obtain a sufficiently dense mesh and it may be used to approximate the limit surface. The refined mesh may include two types of points. The first type may be called vertex points, which are the displacements of the control vertices. The other type may be called edge points, which are the inserted points on edges.

Figure 17:
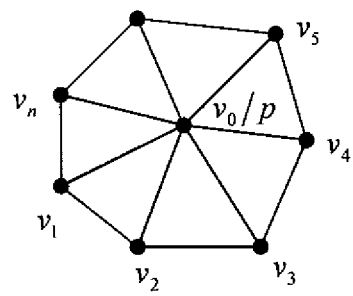
FIG. 17 is an illustration of Loop's evaluation rule for a vertex point in an embodiment of the invention.
Figure 18:
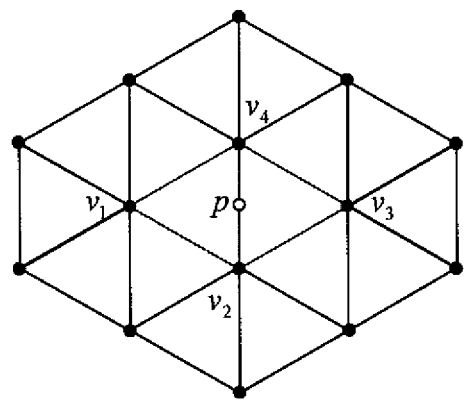
FIG. 18 is an illustration of the modified Loop's evaluation rule for an edge point in an embodiment of the invention.

With Loop's subdivision scheme the limit positions of these points can be explicitly evaluated by some rules. The evaluation rule for a vertex point p with a valence of n as shown in FIG. 17 may be given by $$p = \frac{c_0 v_0 + c_1 v_1 + \ldots + c_n v_n}{c_0 + c_1 + \ldots + c_n}, \tag{45}$$

where $v_0, \ldots, v_n$ are control vertices, $$c_0 = \frac{3}{8} n a/(n) \text{ with } a(n) = \frac{5}{8} - \frac{(3 + 2\cos(2\pi/n))^2}{64},$$
and $c_1 = \ldots = c_n = 1$.

According to the Loop's subdivision rules, the evaluation of an edge point may involve all 2-neighborhood vertices. For an edge point in an ordinary mesh with a valence of six for each vertex, the number of 2-neighborhood vertices is 14. To simplify computation, especially in mesh traversal, one embodiment may only consider 1-neighborhood vertices, which are the four non vertical members immediately surrounding p in FIG. 18. This simplification may provide a good approximation. The approximate evaluation rule for an edge point p may be given by $$p = \frac{c_1 v_1 + c_2 v_2 + c_3 v_3 + c_4 v_4}{c_1 + c_2 + c_3 + c_4}, \tag{46}$$

where $c_1 = c_3 = 15$, and $c_2 = c_4 = 32$.

Loop's subdivision method is an approximating scheme, which may indicate the limit surface may not pass through the control vertices. In the present invention, it implies that the resulting model may pull away from the original scanner data. Therefore, the control vertices may be optimized so that the final model can more accurately approximate the original data. This optimization process may be realized by minimizing the distance between the limit surface and the original data.

The distance can be represented by an energy function as defined by $$E = \sum_i \|q_i - p_i\|^2, \tag{47}$$

where $q_i$ is an original data point, and $p_i$ is its closest point on the limit surface. One can derive that $p_i$ is a weighted combination of the control vertices, i.e., $$p_i = \sum_j w_{i,j} v_j,$$

where the weights $w_{i,j}$ are determined by the projection of $q_i$ on the limit surface and the said evaluation rules. Thus the energy function can be rewritten as $$E = \sum_i \left\| q_i - \sum_j w_{i,j} v_j \right\|^2. \tag{48}$$

In matrix form, $$E = \|Q - WV\|^2 \tag{49}$$

where $Q = [q_i]_{N \times 1}$ is the data vector with N data points assumed, $V = [v_j]_{K \times 1}$ is the vertex vector with K control vertices assumed, and $W = [w_{i,j}]_{N \times K}$ is the weighting matrix. Then the minimization of E may be a least squares problem in nature, and generally equivalent to solving the linear equations $(W_T W)V = W^T Q$. Since $W^T W$ is symmetric, positive-definite and sparse, the equations can be solved efficiently by the conjugate gradient method (e.g., Shewchuk, J. R., "An Introduction to the Conjugate Gradient Method without the Agonizing Pain", Carnegie Mellon University, Pittsburgh, Pa., 1994). As a result, the optimization of V may be achieved by iteratively minimizing E. The least squares minimization is optimal on Gaussian noise, but may be sensitive to outliers. Therefore, those data points which are far away from the limit surface may be rejected. A regularization term (such as a spring model) may be required in the energy function to guarantee a stable solution.

Figure 19:
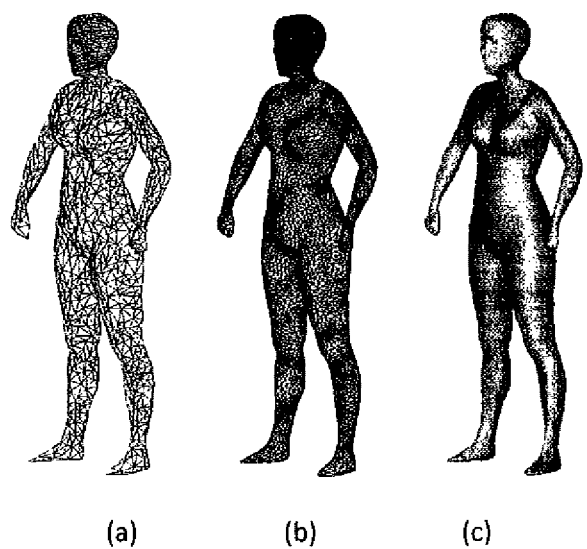
FIGS. 19A-C represent an optimized control mesh, its subdivision mesh, and the shaded model in an embodiment of the invention.

As an example, an optimized subdivision mesh is shown in FIG. 19. The mesh was created by optimizing the control mesh in FIG. 15 fitted with the original data in FIG. 11.

Figure 20:
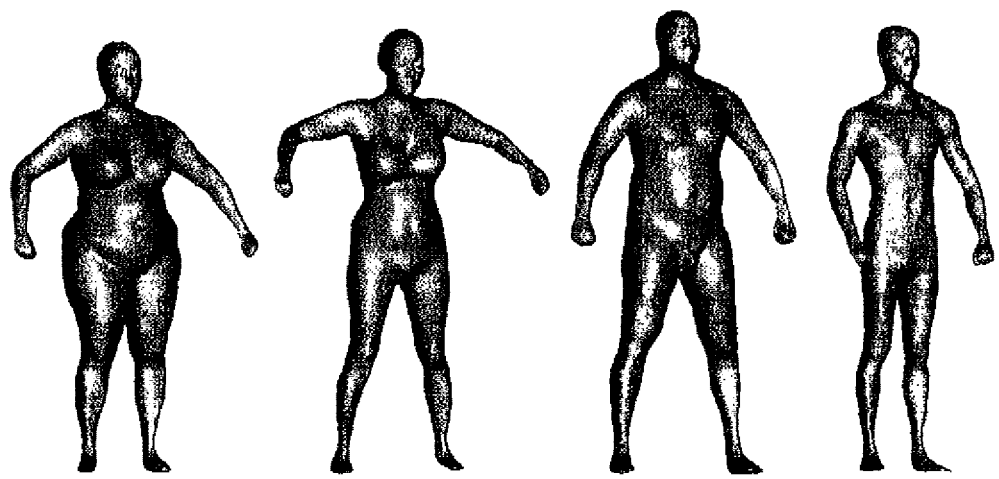
FIG. 20 depicts the reconstructed body models or images of subjects with various shapes and sizes in an embodiment of the invention.
Figure 21:
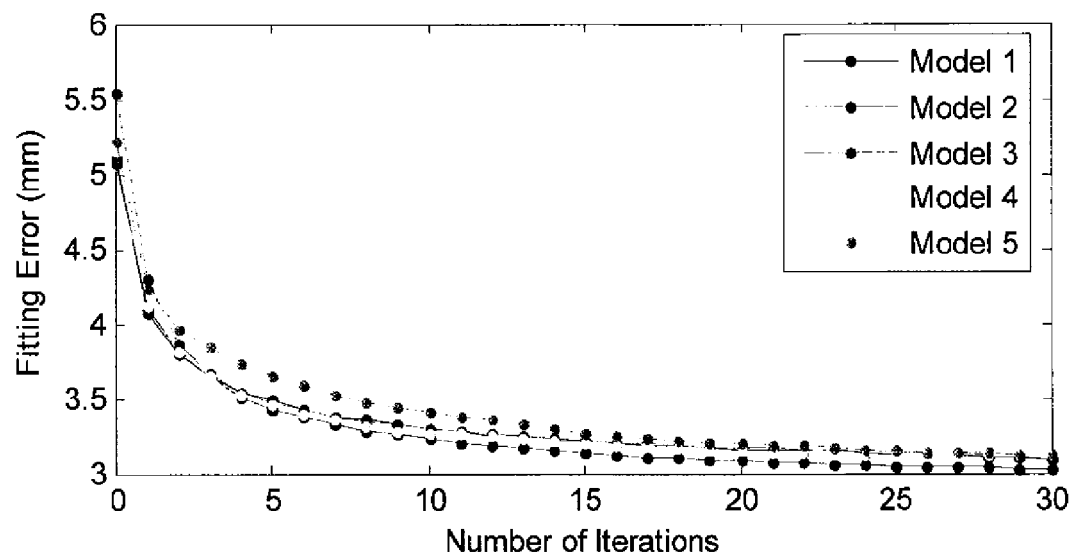
FIG. 21 is a graph that illustrates the performance of mesh optimization in an embodiment of the invention.

Testing an embodiment shows body models of FIG. 20 were obtained by iteratively performing mesh optimization 15 times. The data size and running time on a 2.0 GHz PC for each model are listed in Table 4, where the model in FIG. 19 is labeled as 1, and the models in FIG. 20 are labeled as 2-5. Since only the control mesh needs to be stored in one embodiment of the invention, the final model can be recovered by using the evaluation rules of subdivision surfaces, the data compression ratio (which is defined as the ratio of the size of original data to the size of control mesh) is up to 16. The running times for areas of the method embodiment are shown separately. The method is computationally efficient. The total running time is less than 10 s, and the last step takes most of it. The convergence of mesh optimization is demonstrated in FIG. 21. The modeling accuracy is measured by fitting error which equals $$\sqrt{E/N}, \text{ where } E = \sum_i \|q_i - p_i\|^2$$

is the energy defined in Equation (40), and N is the total number of original data points used for mesh optimization. After 15 iterations, the optimization process has already been very close to convergence, and the fitting error is less than 3.5 mm.

TABLE 4

Data sizes and running times for the presented models.

| | Number of points | | | | Time (s) | | | |
|---|---|---|---|---|---|---|---|---|
| Model | Original | Resampled | Control | Final | 1 & 2 | 3 | 4 | Total |
| 1 | 36,328 | 11,008 | 2,203 | 8,806 | 0.1 | 0.6 | 6.8 | 7.5 |
| 2 | 39,202 | 11,438 | 2,289 | 9,150 | 0.1 | 0.7 | 7.2 | 8.0 |
| 3 | 35,620 | 10,202 | 2,041 | 8,158 | 0.1 | 0.6 | 8.5 | 9.2 |
| 4 | 45,598 | 12,270 | 2,455 | 9,814 | 0.1 | 0.7 | 8.3 | 9.1 |
| 5 | 39,017 | 11,098 | 2,221 | 8,878 | 0.1 | 0.7 | 6.9 | 7.7 |

Figure 22:
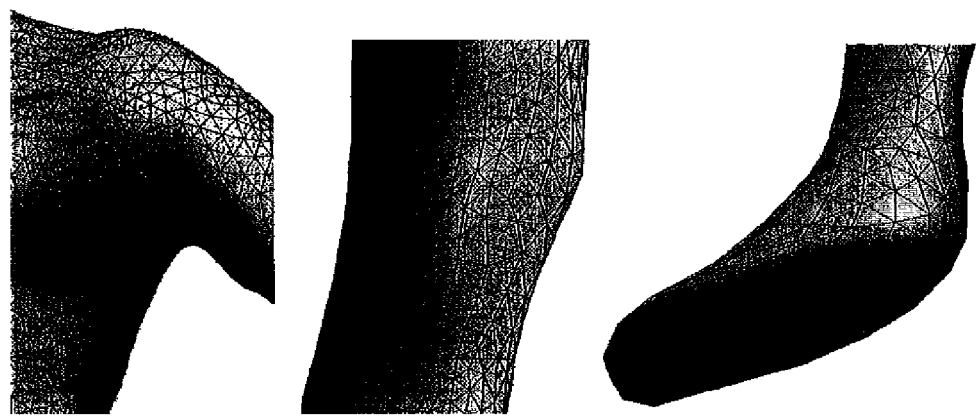
FIGS. 22A-22C are images that show the close-up views of gap and hole filling in an embodiment of the invention.
Figure 23:
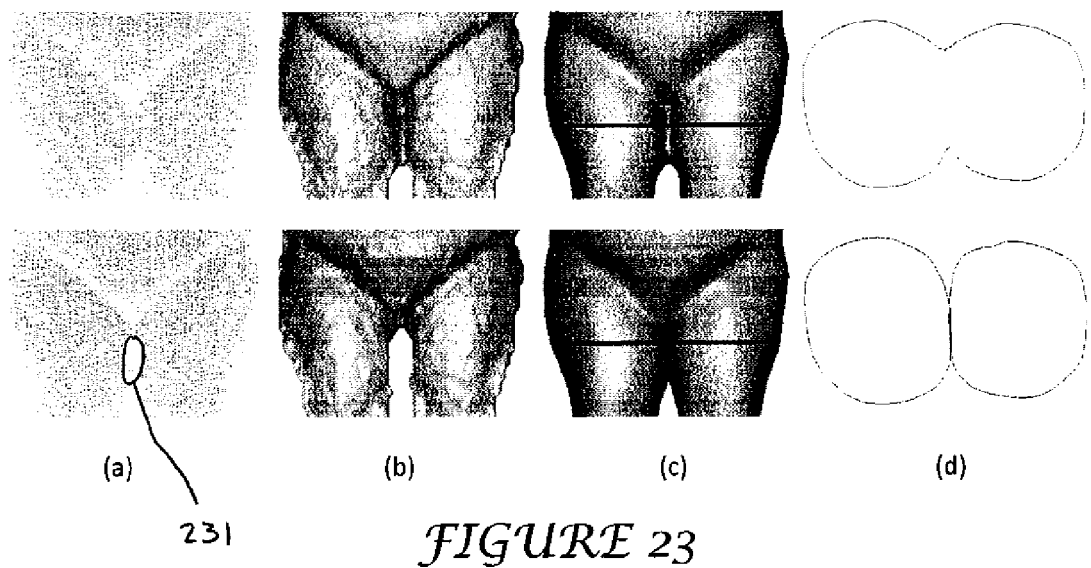
FIGS. 23A-D illustrate the webbing effect before (the first row) and after (the second row) treatment in an embodiment of the invention (original data (a); initial mesh (b); reconstructed surface (c); and contour corresponding to the line in FIG. 23C (d)).

To demonstrate that embodiments of the intention are capable of hole and gap filling, some close-up views of the model from FIG. 19 are shown in FIG. 22. The gap under the armpit has been completed and the holes at the knee and the sole have been filled. It can also be observed that the original data are noisy, but the reconstructed surface is smooth. The foot is a difficult area to be reconstructed, due to the missing data, and high noise and low resolution caused by the long distance from the sensor in our rotary scanner.

As mentioned above, the webbing effect can occur in some areas such as the crotch while modeling overweight subjects. An example is shown in the first row of FIG. 23, where the data is taken from the first subject in FIG. 20. The data resampling and initial mesh generation method may not identify the contact area between the legs, and as a result, the webbing effect may take place in the reconstructed surface. Accordingly, as shown in the second row an embodiment may allow a user to manually mark the crotch area, and temporarily discarded data points in this area (encircled in area 2301) in the initial mesh generation. As a result, the two legs may be separated. The discarded data points may be used later for surface fitting.

Thus, an embodiment of the invention describes a surface reconstruction method for human body modeling from 3D scanner data. It may represent the body with a single subdivision surface so body segmentation can be avoided during the modeling process. In addition to the human body, it is also applicable to other objects. For example, embodiments may work with non-human objects that have scan data that can be separated into two views, and each view can be regarded as samples on a bivariate surface defined in a common projection plane.

For a two-view scanner, large gaps may exist due to the limited field of view. For occlusion areas where the surface viewed on the sagittal plane is almost flat and featureless, embodiments of the present invention can realistically restore smooth and natural body shapes.

An embodiment of the invention may be used for making body measurements. Volume measurement may be performed using a depth buffer of graphics hardware. The depth buffer, also called the z-buffer, may record a depth value for each rendered pixel. With 3D APIs such as OpenGL (D. Shreiner, M. Woo, J. Neider et al., "OpenGL Programming Guide, Version 2.1," Addison-Wesley, Reading, Mass., 2007.), the z-buffer may be switched to keep track of the minimum or maximum depth (distance to the viewport) for each pixel on the screen. To measure the body volume, the 3D body model may be rendered twice in the anterior view using orthographic projection. During the two renderings, the z-buffer may be set to record the minimum and maximum depth of each pixel, respectively. Then the two depth maps may be read from the z-buffer corresponding to the front and back surfaces of the body, respectively. As a result, a thickness map of the body from the difference between the two depth maps may be created. Finally, the body volume may be calculated by integrating over the thickness map based on the known pixel scale.

Z-buffering may be generally equivalent to re-sampling the surface data on a regular grid, and thus the size of the viewport that determines the sampling interval may affect the measure accuracy. However, a moderate size of the viewport such as 500 pixels×500 pixels may be sufficient to reach high accuracy. This technique may be efficient in time cost, as compared to the slice-based methods.

Measured parameters may include circumferences and cross-sectional areas of a number of locations (such as the chest, waist, abdomen, hip, upper thigh, etc.), whole body volume, segmental volumes (such as the abdomen-hip volume and the upper thigh volume), and body surface area.

Anthropometric measures extracted from a 3D body model can be used to assess the overall amount and the distribution of body fat. For example, 3D body measurement can be utilized to assess central obesity, which refers to excessive abdominal fat accumulation. From a 3D body model, waist circumference and waist-hip ratio can be calculated (which may indicators for assessing central obesity). A significant advantage of 3D body measurement is that it is not limited to linear measures such as circumferences. In fact, this technology offers the possibility to derive new central obesity-associated health indexes from higher-dimensional measures such as abdominal volume and waist cross-sectional area.

Whole body volume can be used to estimate percent body fat by using the two-component body model when body weight is also measured. If the body is assumed to be composed of fat and fat-free mass (FFM) and these densities are constant, then the percentage of body fat (% BF) can be calculated by $$\% \ BF = \left(\frac{A}{D_b} - B\right) \times 100, \tag{50}$$

where $D_b$ is the body density (in kg/L) calculated by dividing body weight by whole body volume corrected for lung volume; A and B are derived from the assumed fat density ($D_F$) and FFM density ($D_{FFM}$). $D_F$ is relatively stable and is set usually as 0.9 kg/L. But slightly different values of $D_{FFM}$ appear in the literature. A conventional equation is, $$\% \ BF = \left(\frac{4.95}{D_b} - 4.50\right) \times 100, \tag{51}$$

where $D_{FFM}$=1.1 kg/L is assumed.

Thus, an embodiment includes a portable, economical 3D body imaging system for body composition assessment. Embodiments may be used in clinical and field settings such as physician's offices, mobile testing centers, athletic facilities, and health clubs. Embodiments offer the benefits of low cost, portability, and minimal setup with instantaneous data acquisition. An embodiment may implement methods for system calibration, stereo matching, surface reconstruction, and body measurement. Embodiments may include methods of body fat and anthropometric measurements. Embodiments may be used in public health. For example, new indices for estimation of the distribution of body fat can be utilized for comparisons to biomarkers and subsequent predictions of health risks. Embodiments may also be ideal for monitoring changes in body size and shape over time and exploring possible associations with related health conditions.

Thus, multiple embodiments have been described herein. For example, one embodiment includes determining (a) a front image data set based on stereoscopically imaging a front-side of a subject using first and second front-side digital cameras collectively positioned in a first static position and (b) a back image data set based on stereoscopically imaging a back-side of the subject using first and second back-side digital cameras collectively positioned in a second static position. The data sets may include raw scanned image data, processed image data, resampled image data, and/or combinations thereof. Embodiments may or may not include projecting (a) a front visual pattern on the front-side of the subject to create a front artificial texture using a front projector and (b) projecting a back visual pattern on the back-side of the subject to create a back artificial texture using a back projector. For example, such artificial texturing may be beneficial for some surfaces (e.g., skin) but not as beneficial for other surfaces. Embodiments of the invention are not limited to humans or animals. Embodiments may include determining a mesh, which fills at least a portion of a non-imaged occlusion between the front and back image data sets, based on the front and back image data sets. Thus, such a mesh may merge, zipper, or couple front and back images or meshes across an occluded space such as a person's side when imaged from the front and back but not from the sides. Embodiments may further determine a three-dimensional whole body surface image, without repositioning any of the front-side or back-side cameras, based on any number of factors such as (a) various meshes (e.g., front mesh, back mesh, initial mesh, control mesh, and the like), (b) front and back artificial textures (e.g., random spec patterns, grids, multi-colored spectrums, and the like), and (c) the front and back image data sets.

The front and back cameras may be vertically aligned but are not required to be so oriented. Imaging systems may include various total maximum camera counts, such as two cameras for the front and an addition two cameras for the back. Other embodiments may include four or more cameras for the front and four or more cameras for the back. As used herein, "front" and "back" may include, for example, anterior and posterior images of a human subject but may, in some cases, simply include different view points of a subject separated by occlusions. Thus, embodiments are also suitable to, for example, image the left side (front) and right side (back) of a subject and fill in occlusions there between.

Embodiments may include simultaneously and instantaneously capturing stereoscopic images of the front-side and back-side of the subject using all of the front-side and back-side digital cameras. For example, front cameras may capture an image at the same time the back side cameras take an image. Thus, all cameras in the system may capture their respective images at the same instant in time. However, such simultaneous captures may also include instances where front cameras initiate image capture slightly before or after back cameras initiate image capture, but all cameras may nevertheless still be capturing data at one moment in time. As viewed by those of ordinary skill in the art, generally simultaneous capture may facilitate working with subjects, such as children, that may fidget and have difficulty maintaining a single position during imaging.

Embodiments may include zippering front and back image sets using an Add-Delete method that includes, for example, adding points to a front contour to facilitate zippering (i.e., merging or coupling) the front contour to a back contour, directly or indirectly. Later some of those same added points may be deleted when creating simplified meshes. Embodiments may include soft-deleting aspects where, for example, points are deleted based on weights, such as weights that indicate a point is or is not an original data point. Some embodiments may include subdividing a mesh to fit original image data. For example, equations used in relation to subdivision may include factors based on original image data.

Embodiments may concern passively determining body surface images without use of, for example, laser scanners or structured light. Also, as used herein a determined body surface image includes a body surface model. For example, at various points herein determining an image is used interchangeably with determining a model.

Embodiments may include code to determine (a) front and back image data sets based on stereoscopically imaging a front-side and a back-side of a subject; (b) a mesh, and (c) a three-dimensional whole body surface image. Thus, embodiments do not necessarily need to be involved in actually acquiring original raw image data but may instead by used to merely process previously acquired data.

Figure 24:
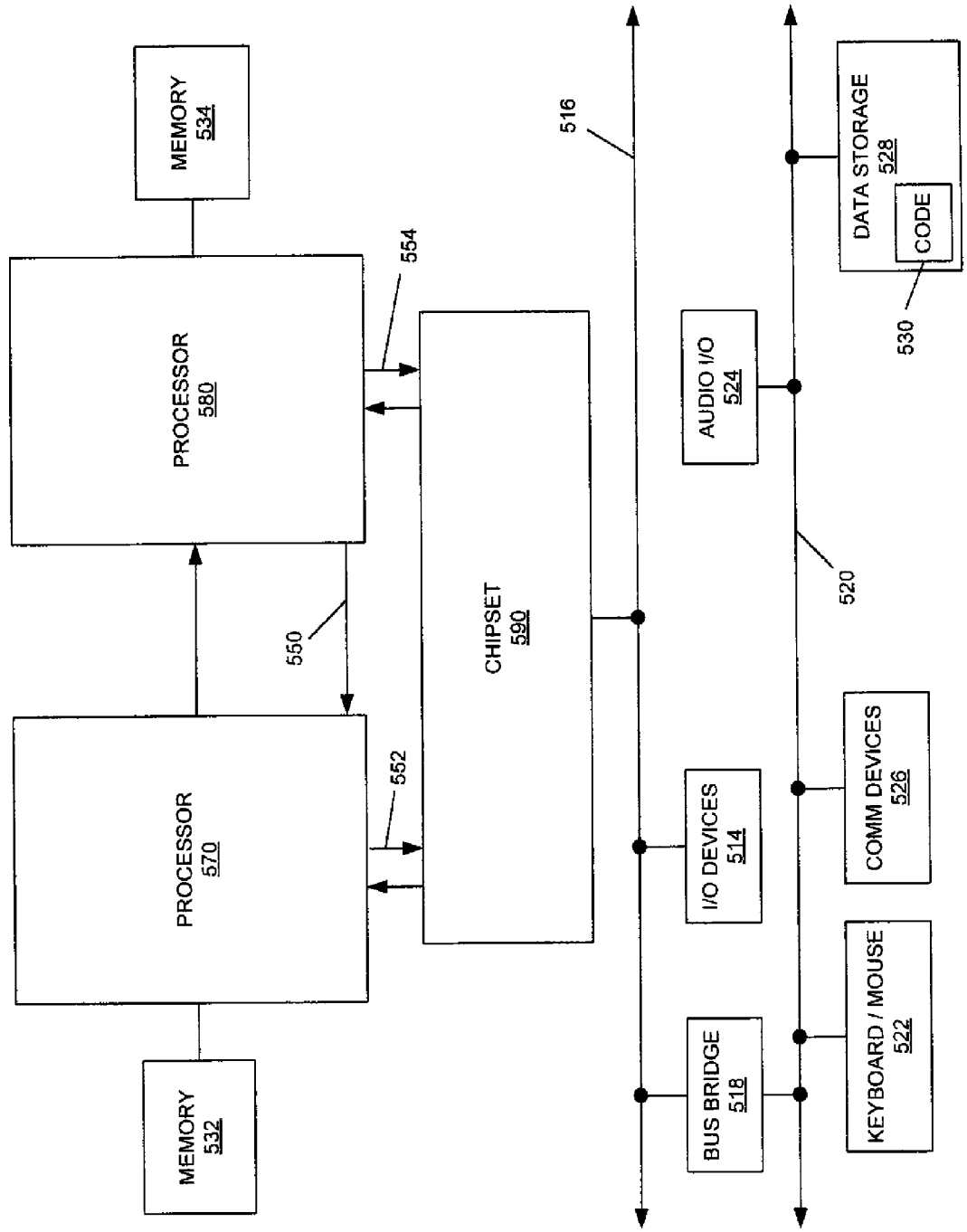
FIG. 24 includes a system for operation with embodiments of the invention.

Embodiments may be implemented in many different system types. Referring now to FIG. 24, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multi-core processors. The term "processor" may refer to any device or portion of a device that processes electronic data from registers and/or memory to transform that electronic data into other electronic data that may be stored in registers and/or memory.

First processor 570 may include a memory controller hub and point-to-point (P-P) interfaces. Similarly, second processor 580 may include a MCH and P-P interfaces. The MCHs may couple the processors to respective memories, namely a memory 532 and a memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces.

Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMS) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. For purposes of this disclosure, the terms "code" or "program" cover a broad range of components and constructs, including applications, drivers, processes, routines, methods, modules, and subprograms. Thus, the terms "code" or "program" may be used to refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
  determining a front image data set based on stereoscopically imaging a front-side of a subject using first and second front-side digital cameras collectively positioned in a first static position;
  projecting a front visual pattern on the front-side of the subject to create a front artificial texture using a front projector;
  determining a back image data set based on stereoscopically imaging a back-side of the subject using first and second back-side digital cameras collectively positioned in a second static position;
  projecting a back visual pattern on the back-side of the subject to create a back artificial texture using a back projector;
  determining a mesh, which fills at least a portion of a non-imaged occlusion between the front and back image data sets, based on the front and back image data sets;
  optimizing a disparity map based on $$E(f) = \sum_{i \in P} D_p(f_p) + \sum_{(p,q) \in N} V_{p,q}(f_p, f_p);$$

and
  determining a three-dimensional whole body surface image, without repositioning any of the front-side or back-side cameras from the first and second static positions, based on the (a) mesh, (b) front and back artificial textures, (c) the front and back image data sets; and (d) the optimized disparity map.

2. The method of claim 1 including simultaneously and instantaneously capturing stereoscopic images of the front-side and back-side of the subject using all of the front-side and back-side digital cameras.

3. The method of claim 1 including determining the three-dimensional whole body surface image at a sub-pixel resolution.

4. The method of claim 1 including zippering the front and back image sets, using an Add-Delete method, to create the mesh.

5. The method of claim 1 including:
  adding points to an edge of one of the front and back image data sets and weighting the added points to determine an initial mesh;
  soft-deleting the weighted added points to determine a control mesh; and
  subdividing the control mesh to determine the mesh.

6. The method of claim 1 including:
  resampling the front image data set, on a front regular grid, to determine a front mesh and resampling the back image data set, on a back regular grid, to determine a back mesh;
  generating an initial mesh that couples the front mesh to the back mesh;
  using soft-deletion to simplify the initial mesh to determine a control mesh; and
  subdividing the control mesh to fit original image data, acquired from the first and second front-side and back-side cameras, and determine the mesh.

7. The method of claim 6 including:
  storing the control mesh into a non-volatile memory included in a computer; and
  discarding the original image data and then discontinuing power to the computer followed by reconstructing the mesh based on the stored control mesh.

8. The method of claim 1 including:
  determining a disparity space image and segmenting the subject from a related background to determine the disparity map; and
  refining the disparity map, via local matching on a pixel-by-pixel basis followed by global optimization, to determine the optimized disparity map;
  wherein the front-side corresponds to an anterior side of the subject and the back-side corresponds to a posterior side of the subject.

9. The method of claim 1 including, based on the three-dimensional whole body surface image, determining one or more of the following parameters for the subject including body volume, obesity, medication dosage, and body fat.

10. An article comprising a non-transitory medium storing instructions that enable a processor-based system to:
  determine front and back image data sets based on a stereoscopically imaged front-side and back-side of a subject respectively imaged using first and second front-side digital cameras collectively positioned in a first static position and first and second back-side digital cameras collectively positioned in a second static position;
  determine a mesh, which fills at least a portion of a non-imaged occlusion between the front and back image data sets, based on the front and back image data sets; and
  optimize a disparity map based on $$E(f) = \sum_{i \in P} D_p(f_p) + \sum_{(p,q) \in N} V_{p,q}(f_p, f_p);$$

determine a three-dimensional whole body surface image, without having repositioned any of the front-side or back-side cameras from the first and second static positions, based on the (a) mesh, (b) the front and back image data sets, and (c) the optimized disparity map.

11. The article of claim 10 storing instructions that enable the system to determine the three-dimensional whole body surface image based on having used a total maximum plurality of cameras that does not exceed eight cameras.

12. The article of claim 10 storing instructions that enable the system to zipper the front and back image sets, using an Add-Delete method, to create the mesh.

13. An apparatus comprising:
a non-transitory memory to receive image data;
a processor, coupled to the memory, to determine (a) front and back image data sets based on stereoscopically imaging a front-side and a back-side of a subject respectively using first and second front-side digital cameras collectively positioned in a first static position and first and second back-side digital cameras collectively positioned in a second static position; (b) a mesh, which fills at least a portion of a non-imaged occlusion between the front and back image data sets, based on the front and back image data sets; an optimized disparity map based on $$E(f) = \sum_{i \in P} D_p(f_p) + \sum_{(p,q) \in N} V_{p,q}(f_p, f_p);$$

and (c) a three-dimensional whole body surface image, without repositioning any of the front-side or back-side cameras from the first and second static positions, based on the mesh, the optimized data map, and the front and back image data sets.

14. The apparatus of claim 13, wherein the apparatus is portable.

15. The apparatus of claim 14, wherein the apparatus includes a total maximum plurality of cameras that does not exceed four cameras.

16. The apparatus of claim 13, wherein processor is to, based on the three-dimensional whole body surface image, determine one or more of the following parameters for the subject including body circumference, body volume, obesity, medication dosage, body fat, and apparel sizing.

17. The apparatus of claim 13, wherein the apparatus is configured to passively determine the three-dimensional whole body surface image.

* * * * *

UNITED STATES PATENT AND TRADEMARK OFFICE
CERTIFICATE OF CORRECTION

PATENT NO. : 8,823,775 B2  
APPLICATION NO. : 12/771565  
DATED : September 2, 2014  
INVENTOR(S) : Bugao Xu et al.

Page 1 of 1

It is certified that error appears in the above-identified patent and that said Letters Patent is hereby corrected as shown below:

In the Specification

Col. 1:
Lines 16-18,

"The U.S. Government may have certain rights in this invention pursuant to Contract No. 1R21DK081206-01 awarded by the NIH."

should be

--This invention was made with government support under Grant no. R21 DK081206 awarded by the National Institutes of Health. The government has certain rights in the invention.--

Signed and Sealed this  
Twenty-sixth Day of May, 2015

Michelle K. Lee  
*Director of the United States Patent and Trademark Office*